US011275096B2

(12) United States Patent
Musci

(10) Patent No.: US 11,275,096 B2
(45) Date of Patent: Mar. 15, 2022

(54) BLOOD TRANSFER DEVICES AND METHODS THEREOF

(71) Applicant: BIOCERYX TECHNOLOGIES INC., Menlo Park, CA (US)

(72) Inventor: Thomas J. Musci, Redwood City, CA (US)

(73) Assignee: BIOCERYX TECHNOLOGIES INC., Menlo Park, CA (US)

( * ) Notice: Subject to any disclaimer, the term of this patent is extended or adjusted under 35 U.S.C. 154(b) by 249 days.

(21) Appl. No.: 15/993,235

(22) Filed: May 30, 2018

(65) Prior Publication Data

US 2019/0094254 A1 Mar. 28, 2019

Related U.S. Application Data

(60) Provisional application No. 62/564,684, filed on Sep. 28, 2017.

(51) Int. Cl.
   *G01N 35/10* (2006.01)
   *G01N 33/49* (2006.01)
   *B01L 3/00* (2006.01)

(52) U.S. Cl.
   CPC .......... *G01N 35/1079* (2013.01); *B01L 3/563* (2013.01); *G01N 33/491* (2013.01); *B01L 2200/026* (2013.01); *B01L 2300/0672* (2013.01)

(58) Field of Classification Search
   None
   See application file for complete search history.

(56) References Cited

U.S. PATENT DOCUMENTS

| 3,585,984 A | 6/1971 | Buchanan |
| 4,342,341 A | 8/1982 | Lee |

(Continued)

FOREIGN PATENT DOCUMENTS

| JP | 2015036046 A | 2/2015 |
| WO | WO 2011/004360 A1 | 1/2011 |

OTHER PUBLICATIONS

USPTO. International Search Report and Written Opinion dated Dec. 17, 2018, for related counterpart PCT Application No. PCT/US2018/052264 (BioCeryx Inc.), 8 pages.

(Continued)

*Primary Examiner* — Daniel S Larkin
(74) *Attorney, Agent, or Firm* — Baker Botts L.L.P.

(57) ABSTRACT

Embodiments in accordance with the present disclosure are directed to blood transfer apparatuses, sleeve-puncturing assemblies, and methods thereof. An example blood transfer apparatus includes a sleeve-puncturing assembly comprising a sleeve and a hollow conduit. The sleeve is configured and arranged with longitudinal portions to be placed over or engage a blood collection container. The sleeve has an open end that engages with a portion of the blood collection container and another end that provides containment of the blood collection container while the open end is engaged with the portion of the blood collection container. The sleeve further includes a lateral portion to provide support the hollow conduit. The hollow conduit and the longitudinal portions of the sleeve engage with the blood collection container and a blood collection container to provide sufficient pressure while engaged to pull a predetermined amount of plasma or serum from the blood collection container.

15 Claims, 12 Drawing Sheets

(56) References Cited

U.S. PATENT DOCUMENTS

| | | | |
|---|---|---|---|
| 4,378,812 A * | 4/1983 | Sarstedt | A61B 5/150236 |
| | | | 600/578 |
| 4,443,220 A | 4/1984 | Hauer et al. | |
| 4,459,997 A * | 7/1984 | Sarstedt | B01L 3/0217 |
| | | | 422/918 |
| 5,086,783 A * | 2/1992 | Macors | A61M 5/31511 |
| | | | 600/578 |
| 5,207,638 A | 5/1993 | Choksi et al. | |
| 5,270,219 A | 12/1993 | DeCastro et al. | |
| 5,324,256 A | 6/1994 | Lynn et al. | |
| 5,603,530 A | 2/1997 | Guest | |
| 5,743,861 A | 4/1998 | Columbus et al. | |
| 6,905,561 B2 | 6/2005 | Jones et al. | |
| 10,293,338 B2 * | 5/2019 | Foucault | G01N 33/491 |
| 2002/0169408 A1 | 11/2002 | Beretta et al. | |
| 2002/0183651 A1 | 12/2002 | Hyun | |
| 2003/0069538 A1 | 4/2003 | Pfeifer et al. | |
| 2004/0071786 A1 | 4/2004 | Grippi et al. | |
| 2005/0139547 A1 | 6/2005 | Manoussakis et al. | |

OTHER PUBLICATIONS

Supplementary European Search Report dated Jun. 9, 2021 in Application No. EP18862866.

* cited by examiner

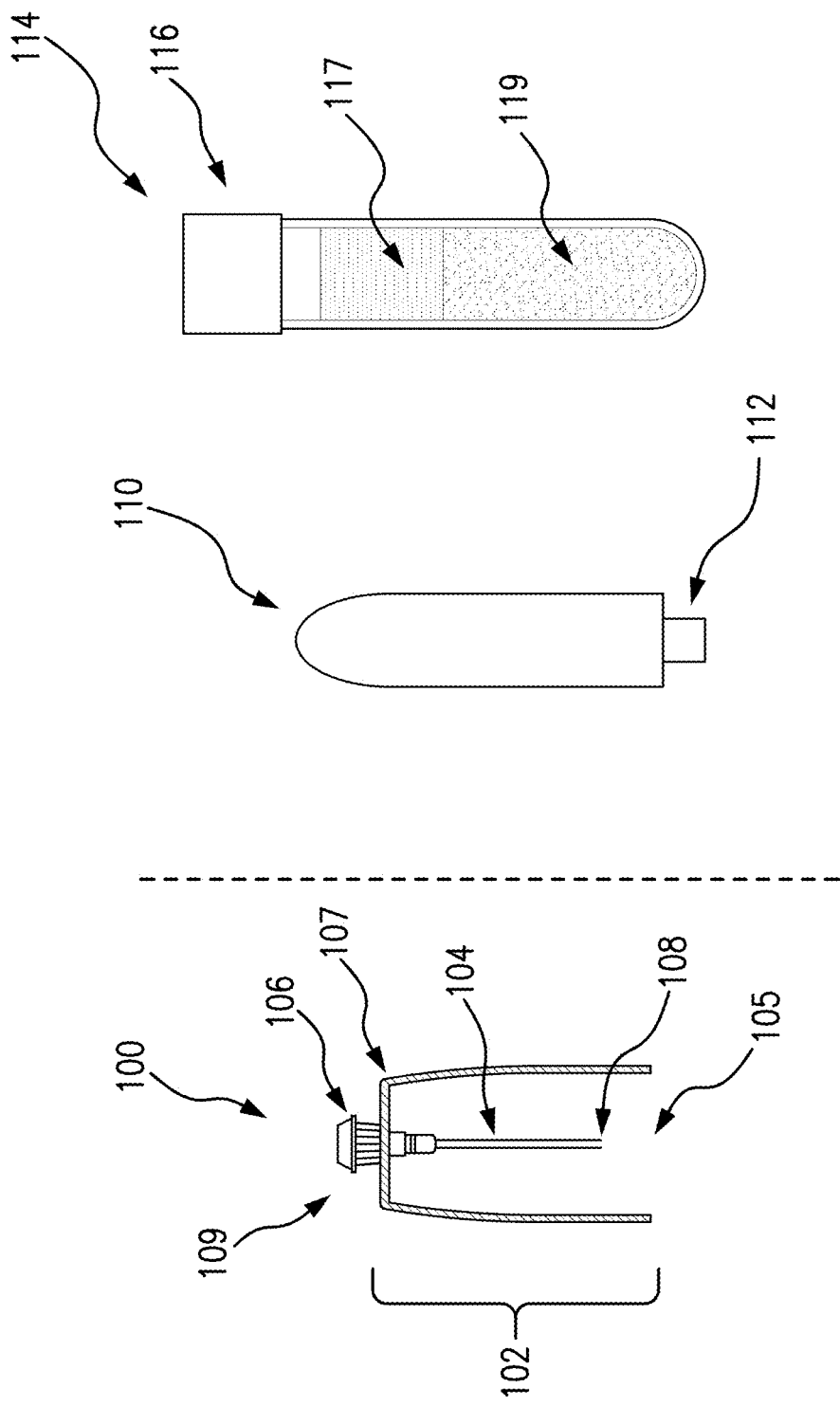

BLOOD TRANSFER DEVICES AND METHODS THEREOF

OVERVIEW

Various embodiments in accordance with the present disclosure are directed to blood transfer devices, sleeve-puncturing assemblies and methods thereof that are used to transfer a predetermined amount of a component, e.g., plasma or serum, of a blood sample from an enclosed blood collection container to an enclosed blood transfer container.

It can be advantageous for diagnosis of diseases, physiological conditions, storage, and other purposes to collect and transfer blood from an organism to different containers for further analysis and/or testing. Transferring the blood, such as plasma or serum, to another container can expose a user or surrounding area to contamination. For example, the blood in a gross or droplet form might contain infectious particles (e.g., virus, bacteria) or genetic material (e.g., nucleic acids) and can cause contamination of surrounding area(s), to the user operating the transfer, or to others in the area. Contamination can cause a variety of issues. Contamination of the surrounding area with deoxyribonucleic acid (DNA) may cause erroneous diagnosis results. For example, contamination of the surrounding areas can result in inadvertent mixing of DNA from more than one individual in a molecular assay. There can also be requirements for specific expertise in handling open containers of human or animal blood, which can increase costs of testing. For example, spilling the blood can cause the above-described contamination risk and also risk loss of valuable blood sample.

In accordance with aspects of the present disclosure, the sleeve-puncturing assembly, blood transfer apparatuses and techniques described herein can be used to transfer a component of a blood sample from a blood collection container to a blood transfer container. A blood transfer apparatus, which includes a sleeve-puncturing assembly, according to specific embodiments, draws a predetermined volume of plasma or serum so that a user does not have to measure the volume and which allows the user to transfer the blood without opening either container. The sleeve-puncturing assembly can engage (e.g., connect to) both the containers. The above-noted embodiments and others implements a blood transfer container sealed with negative pressure inside, e.g., air pressure or vacuum pressure, which can be referred to as "loaded with vacuum." The negative pressure is sufficient to pull the predetermined volume of plasma or serum into the blood transfer container. In some specific aspects, once the negative pressure is set, the blood transfer container may be without any pressure-adjusting mechanism, outside of removing or puncturing the upper portion (e.g., top) of the blood transfer container sufficient to expose the blood transfer container to atmospheric pressure or other pressures. In other aspects, the blood transfer container includes a pressure-adjusting mechanism (e.g., a plunger) used to generate the negative pressure and to draw the plasma or serum on-the-fly, as further described below. In order to draw the plasma or serum, a user or an automated arm (e.g., robotic) can place the sleeve-puncturing assembly on top of the blood collection container that has been centrifuged and inserts the blood transfer container with the negative pressure into the sleeve-puncturing assembly. Engaging the sleeve-puncturing assembly with both the blood collection container and the blood transfer container automatically causes fluid (plasma or serum) to be drawn into the blood transfer container. To complete the transfer, the user or automatic arm does not take the cap (e.g., top) off of the blood collection container or the blood transfer container, nor does the user or automated arm have to pipette the plasma or serum component from the separated blood. Further, the plasma or serum is pulled into the sealed blood transfer container, which can mitigate risk of exposure to the blood to the user and/or the surrounding environment.

In specific aspects, the blood transfer apparatus includes a sleeve-puncturing assembly comprising a sleeve and a hollow conduit, such as a hollow needle. The sleeve can be a cylindrical barrel having an open end for receiving a blood collection container and another end (that may be at least partially-closed or open) for receiving a blood transfer container. The sleeve is hollow and configured to be placed over or engage with a blood collection container. More specifically, the sleeve has longitudinal portions (e.g., walls) that are placed over or engage with the blood collection container and the open end engages with a portion of the blood collection container. The other end provides containment of the blood collection container while the open end is engaged with the portion of the blood collection container. For example, the other end of the sleeve can be at least partially enclosed such that the sleeve forms a tube that is open on one end and enclosed or at least partially enclosed on the other. The sleeve further includes a lateral portion (e.g., the other end, a collar, and/or other types of supports) that provides support for the hollow conduit. For example, the hollow conduit can be coupled to or affixed to the sleeve, and has a first end and a second end. In other specific aspects useful with the above-noted embodiments and other embodiments, the hollow conduit can be permanently affixed to the other end of the sleeve and/or an interior surface of the sleeve, and/or once affixed, may not be removed or otherwise retracted. The hollow conduit and the longitudinal portions of the sleeve are configured and arranged to engage with the blood collection container and to provide sufficient negative pressure while engaged to pull a predetermined amount of plasma or serum from the blood collection container.

In some specific embodiments, the first end of the hollow conduit is arranged to pierce an upper portion of the blood collection container, which is herein interchangeably referred to as "a top", and to contact a portion of a blood sample contained within the blood collection container when the longitudinal portions are placed over or engage with the blood collection container. The second end of the hollow conduit is arranged to pierce an upper portion of a blood transfer container, which is herein interchangeably referred to as "a top", when the blood transfer container is inserted into the sleeve-puncturing assembly. In specific aspects, the hollow conduit is a double pointed needle. The blood transfer container, as described above, has negative pressure inside that is sufficient (e.g., is a set amount of negative pressure) to pull a predetermined amount of plasma or serum from the blood collection container. More specifically, the upper portions of the blood collection container and the blood transfer container can include sealed stoppers formed of a rubber or other type of elastomer that maintain seal of the blood collection container and the blood transfer container. The sealed stopper of the blood transfer container can maintain the negative pressure inside the blood transfer container. To interact with both containers, the hollow conduit extends into the interior space of the sleeve and toward the open end of the sleeve, and through the other end of the sleeve.

In related aspects, the ends of the hollow conduit are contained by the sleeve-puncturing assembly to mitigate risk of a user contacting the ends. For example, the sleeve has longitudinal portions (e.g., walls) that extend from the other end to the open end of the sleeve. The longitudinal portions (e.g., walls) of the sleeve can extend past (e.g., farther) the first end of the hollow conduit, which extends into the interior space of the sleeve and thus the sleeve contains the first end of the hollow conduit. In various aspects, the second end of the hollow conduit extends past the other end of the sleeve. The sleeve-puncturing assembly can include a collar to contain the second end of the conduit. The collar can include a cylinder (or other shaped) collar that is shaped to engage (e.g., connect to) to the blood transfer container and that is affixed to the other end of the sleeve. For example, the collar is hollow and shaped to connect to the blood transfer container. The second end of the hollow conduit extends through the other end of the sleeve and within the hollow portion of the collar. The collar can extend past the second end of the conduit, extending away from the other end of the sleeve, and thereby containing the second end of the hollow conduit.

In related embodiments and/or in addition, the open end of the sleeve can have a plurality of protrusions that jut out from the longitudinal portions (e.g., toward hollow portion) of the sleeve and toward a center portion of the sleeve. The protrusions can include (triangular-shaped) teeth that are arranged about the circumference of the sleeve proximal to the open end, and, in various more-specific aspects, are uniformly spaced about the circumference of the sleeve proximal to the open end. The protrusions can flex in response to force exerted in a first direction and resist flexing in response to another force exerted in a second direction opposite the first. For example, responsive to a force exerted on the protrusions in a direction toward the other end of the sleeve, the protrusions flex. In response to a force exerted on the protrusions in a direction toward the open end of the sleeve, the protrusions resist flexing. The protrusions can flex to allow the sleeve-puncturing assembly to pass over the upper portion of the blood collection container. If the user or automated arm attempts to remove the sleeve-puncturing assembly from the blood collection container, the protrusions may not flex or may resist flexing, which can prevent or mitigate removal of the sleeve-puncturing assembly from the blood collection container. As the protrusions can prevent or mitigate removal of the sleeve-puncturing assembly, a user or automated arm can be prevented from and/or avoid accidental removal of the sleeve-puncturing assembly and/or avoid contact with the hollow conduit therein.

In another alternative embodiment or as a supplemental feature, embodiments include at least one protrusion situated at the open end of the sleeve that may be coupled to the longitudinal portions and proximal to the open end. The at least one protrusion is formed as a wedge with a protruding edge angled inward toward the center portion (e.g., a center of the circumference of hollow portion) of the sleeve and downward away from the other end of the sleeve (e.g., toward the open end). For example, the at least one protrusion generates a taper at the open end of the sleeve proximal to a hollow portion of the sleeve (e.g., an internal space or internal surface of the longitudinal portions). The at least one protrusion can allow for the sleeve-puncturing assembly to be easily guided over the blood collection container but not as easily removed from the blood collection container due to the wedge tips. In various specific embodiments, the at least one protrusion includes one protrusion that is arranged around the circumference of the open end of the sleeve that can form the tapered open end having the wedge angled inward and downward. In other specific embodiments and or in addition, a plurality of stacked protrusions can be used.

In other specific embodiments, the sleeve-puncturing assembly includes an additional sleeve having longitudinal portions (e.g., walls) that extend from the other end of the sleeve and in an opposite direction as the open end. The additional sleeve includes an additional open end that encloses the second end of the hollow conduit (e.g., the walls extend to the additional open end and a greater distance than the second end of the hollow conduit) and which receives the blood transfer container. In other embodiments, sleeve-puncturing assembly may include one sleeve that has two open ends. The hollow conduit can be affixed within the sleeve via the at least one lateral portion and extends proximally within the sleeve. For example, the hollow conduit is affixed to the sleeve via a plurality of supports (e.g., beams) that are coupled to an interior surface of the sleeve on one end and coupled to the hollow conduit on another end. A plurality of supports, which may form a cross-shape (e.g., an "X" shape with the hollow conduit in the middle of the "X"), can be used.

In other aspects, one or more of the first and second ends of the hollow conduit are not enclosed by components of the sleeve-puncturing assembly. For example, the longitudinal portions (e.g., walls) of the sleeve can extend past the first end of hollow conduit and the sleeve-puncturing assembly may not include the collar. A removable cap (e.g., formed of plastic or other material) can be placed over the second end of the hollow conduit to enclose the second end, and which is removed prior to engaging (e.g., coupling) the sleeve-puncturing assembly with the blood transfer container. In another aspect, the sleeve-puncturing assembly includes the collar, which encloses the second end of the hollow conduit, and the longitudinal portions of the sleeve do not extend past the first end of the hollow conduit. A removable cap can be placed over the first end of the hollow conduit, and which is removed prior to placing the sleeve-puncturing assembly over the blood collection container. In other aspects, the sleeve-puncturing assembly does not include the collar and the longitudinal portions (e.g., walls) of the sleeve do not extend past the first end of the hollow conduit. A first removable cap can be placed over the first end of the hollow conduit and a second removable cap can be placed over the second end of the hollow conduit. The removable caps are removed prior to placing the sleeve-puncturing assembly over or engaging with the blood collection container and prior to engaging the sleeve-puncturing assembly with the blood transfer container.

In various aspects consistent with one or more of the above-described embodiments, the negative pressure is generated using the blood transfer container. For example, the blood transfer container can include a (cylinder) barrel with a plunger (or piston) on one end and another end for engaging the sleeve-puncturing assembly, as described-above. The other end includes an upper portion, such as a nozzle or top (e.g., a sealed top), arranged to engage with the other end of the hollow conduit of the sleeve-puncturing assembly. For example, the nozzle or top is sized to be inserted over the other end of the hollow conduit or the collar of the sleeve-puncturing assembly. Once the blood transfer container is engaged (e.g., coupled to) with the sleeve-puncturing assembly or prior to, a user (or automated arm) pulls the plunger (or piston) in a direction away from the nozzle or top of the barrel and which generates the negative pressure inside the blood transfer container. The user can change the amount of negative pressure, and the corresponding amount of plasma or serum drawn, on-the-fly and/or during sample collection. The amount of negative pressure inside the blood transfer container and the resulting amount of plasma or blood drawn can be based on how far the user pulls the plunger (or piston). The barrel of the blood transfer container can further include visual markings to indicate the amount of plasma or blood drawn. And, the nozzle or top can be configured to contain the plasma or blood drawn inside the barrel once drawn.

In other specific aspects, a blood transfer apparatus includes the above described sleeve-puncturing assembly and the blood transfer container. The blood transfer container (plasma collector) has an upper portion (e.g., top) that maintains the negative pressure, such as a vacuum blood tube. As previously described, the sleeve-puncturing assembly includes a sleeve and a hollow conduit. The sleeve is arranged with longitudinal portions to be placed over or engage a blood collection container. For example, the sleeve has an open end to engage with a portion (e.g., the upper portion and/or additional portions) of the blood collection container and another end. The other end provides containment of the blood collection container while the open end is engaged with the portion of the blood collection container. The sleeve further includes a lateral portion (e.g., the other end, the collar or other types of supports) to provide support for the hollow conduit. The hollow conduit and the longitudinal portions of the sleeve are configured and arranged to engage the blood collection container and the blood transfer container, and while engaged, to pull a predetermined amount of plasma or serum from the blood collection container based on the negative pressure inside the blood transfer container.

The hollow conduit, which can be coupled to the sleeve, has a first end and a second end. The first end of the hollow conduit is configured and arranged to pierce an upper portion of the blood collection container and to contact a portion of a blood sample contained within the blood collection container. For example, the hollow conduit can extend 2.95 inches from the top of the collar to the first end for a blood collection container that is configured to collect 10 milliliter (ml) of blood. The second end of the hollow conduit is configured and arranged to pierce an upper portion of the blood transfer container, and thereby cause the blood transfer container to pull a predetermined amount of plasma or serum from the blood collection container. In some aspects, the blood transfer apparatus can further include the blood collection container containing the blood sample. The blood sample can be separated into layers of plasma or serum and cell fraction.

Both the blood collection container and the blood transfer container can include enclosed tubes having upper portions, such as tops. For example, the blood transfer container includes a sealed upper portion that can be pierced by the second end of the hollow conduit, thereby resulting in the negative pressure causing the plasma or serum to be pull therein. The blood collection container can also have a sealed upper portion top used to maintain the blood sample within.

As previously described, in various specific embodiments, the sleeve-puncturing assembly includes a collar affixed to the other end of the sleeve. The collar engages (and/or couples to) the blood transfer container and contains the second end of the hollow conduit. The sleeve can be placed over the blood collection container. In response, the longitudinal portions (e.g., walls) of the sleeve extend from the upper portion of the blood collection container toward (but not to) a bottom portion of the blood collection container. The first end of the hollow conduit extends into an interior space of the blood collection container sufficient to contact plasma or serum of the blood sample. And, the hollow conduit does not extend or otherwise contact the cell fraction of the blood sample. For example, responsive to the sleeve being placed over the blood collection container, the first end of the hollow conduit pierces the upper portion of the second blood collection container and is in contact with the plasma or serum of the blood sample. Responsive to the blood transfer container engaging and/or being in contact with the collar, the second end of the hollow conduit pierces the upper portion of the blood transfer container. The blood transfer container pulls the predetermined amount of the plasma or serum from the blood collection container based on the pressure.

The above-described devices and apparatuses can be used to transfer blood between containers in a manner that can mitigate or prevent contamination. An example method of using such devices and/or apparatuses can include placing a sleeve-puncturing assembly over or engaging with a blood collection container containing plasma or serum separated from cell fraction, thereby piercing a sealed upper portion of the blood collection container with a first end of a hollow conduit and contacting the plasma or serum with the first end of the hollow conduit. As previously described, the sleeve-puncturing assembly includes a sleeve having an open end and another end, and a hollow conduit is supported by a lateral portion of the sleeve (e.g., can be coupled to the other end, a collar, and/or supports of the sleeve) and has the first end and the second end. The method further includes engaging the sleeve-puncturing assembly with a blood transfer container while the first end of the hollow conduit is in contact with the plasma or serum, the blood transfer container having another sealed upper portion to seal a negative pressure inside which is sufficient to pull a predetermined amount of plasma or serum from the blood collection container. In response to the collar engaging (e.g., connecting) the blood transfer container, the method includes piercing the other sealed upper portion of the blood transfer container with the second end of the hollow conduit and pulling the predetermined amount of plasma or serum into the blood transfer container from the blood collection container via the pressure.

Another specific example method can include collecting a blood sample in a blood collection container having a sealed upper portion, and separating cell fraction from plasma or serum of the blood sample, such as by centrifuging the blood sample in the blood collection container. A user or automated arm can place (or otherwise engage) a sleeve-puncturing assembly, as described above, over the blood collection container, thereby piercing the sealed upper portion of the blood collection container with a first end of a hollow conduit and contacting the plasma or serum with the first end of the hollow conduit. While contacting the plasma or serum with the first end of the hollow conduit, the user or automated arm can engage the collar to a blood transfer container. As previously described, the blood transfer container has another sealed upper portion and with pressure inside the blood transfer container that is sufficient to pull a predetermined amount of plasma or serum from the blood collection container. In response to the collar engaging with the blood transfer container, the method further includes piercing the other sealed upper portion of the blood transfer container with the second end of the hollow conduit, and pulling the predetermined amount of plasma or serum into the blood transfer container from the blood collection container via the negative pressure. Although method embodiments are not so limited and may include subsets of the above-listed steps.

The above discussion is not intended to describe each embodiment or every implementation of the present disclosure. The figures and detailed description that follow also exemplify various embodiments.

BRIEF DESCRIPTION OF THE FIGURES

Various example embodiments may be more completely understood in consideration of the following detailed description in connection with the accompanying figures, which form part of this patent document.

FIG. 1A illustrates a sleeve-puncturing assembly, in accordance with various embodiments of the present disclosure;

Figure 1B:
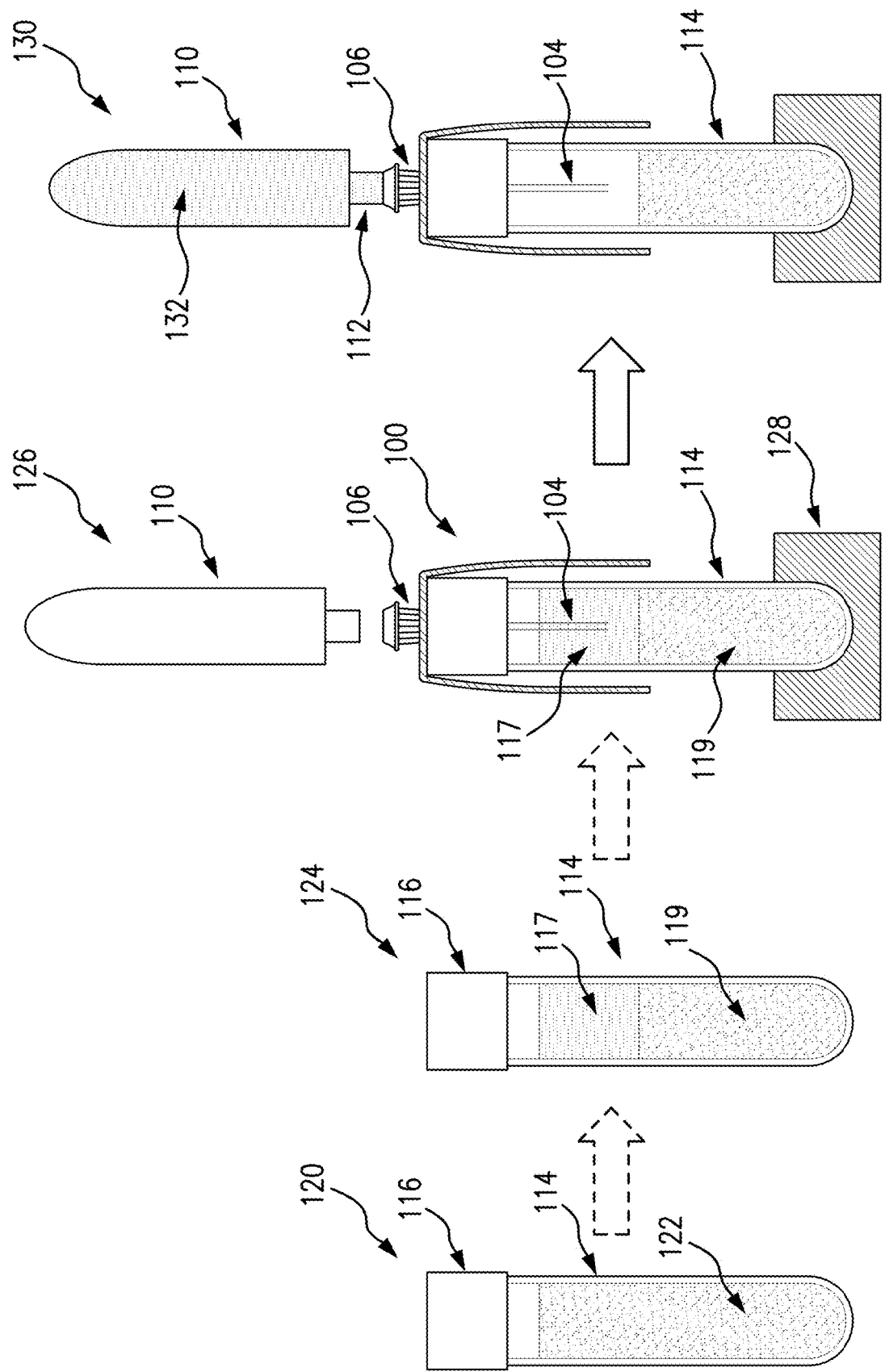
FIG. 1B illustrates an example method for transferring blood from a blood collection container to a blood transfer container, in accordance with various embodiments of the present disclosure.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects as characterized generally or specifically in the exemplary embodiments, claims and/or related aspects illustrated and/or described.

DETAILED DESCRIPTION

Embodiments in accordance with the present disclosure are useful for transferring a predetermined amount of a blood sample from an enclosed blood collection container to an enclosed blood transfer container. In specific embodiments, a user or automated arm can transfer plasma or serum from the blood collection container without removing an upper portion of the blood collection container and without the user actively drawing plasma or serum into a test or storage tube. The blood transfer apparatus, in accordance with a number of embodiments, can pull a predetermined amount of the blood sample into the blood transfer container without the user or other circuitry measuring a specific amount of plasma or serum. While not necessarily so limited, various aspects of the invention may be appreciated through a discussion of examples in this regard.

Accordingly and in the following description, various specific details are set forth to describe specific examples presented herein. It should be apparent to one skilled in the art, however, that one or more other examples and/or variations of these examples may be practiced without all the specific details given below. In other instances, well known features have not been described in detail so as not to obscure the description of the examples herein. For ease of illustration, the same reference numerals may be used in different diagrams to refer to the same elements or additional instances of the same element.

Blood samples can be used for a variety of diagnostic, experimentation or laboratory purposes, such as storage and/or for transfusions, among other uses. A blood sample can be collected from an organism, such as a human or other animal, and used for its intended purposes. Once collected, the blood can be transferred from the container used to collect the blood, herein referred to as the "blood collection container," to another container, herein referred to as the "blood transfer container." Transferring the blood can potentially expose the environment and/or the user that is transferring the sample to the blood. A blood transfer apparatus, in accordance with various embodiments, pulls blood from the blood collection container to the blood transfer container and can mitigate contamination, of the user or surrounding area, from the blood sample. Furthermore, the blood transfer container pulls (e.g., automatically and/or without a user measuring) a predetermined amount of the blood sample. In some embodiments, the user does have to measure, or have the skills to accurately measure and collect, the predetermined amount. In various embodiments, the blood transfer apparatus includes a sleeve-puncturing assembly, and optionally, the blood transfer container and the blood collection container. The sleeve-puncturing assembly is placed on the top of or otherwise engages the blood collection container that contains a blood sample and which results in part of the sleeve-puncturing assembly contacting a component of the blood sample. The blood transfer container is then inserted into the sleeve-puncturing assembly which results in fluid, e.g., plasma or serum, being pulled into the blood transfer container from the blood collection container. The blood component is pulled without removal of the upper portions (e.g., tops) of either container and can thereby reduce contamination risk to the user and others in the surrounding environment.

In a number of embodiments, the sleeve-puncturing assembly includes a sleeve and a hollow conduit. The sleeve can be a cylindrical barrel having an open end for receiving a blood collection container and another end (that may be enclosed or open) for receiving a blood transfer container. For example, the sleeve has longitudinal portions (herein interchangeably referred to as "walls") that are arranged to be placed over or otherwise engage the blood collection container. The open end of the sleeve engages with a portion (e.g., the upper portion) of the blood collection container. The other end, which may be at least partially closed or open, provides containment of the blood collection container while the open end is engaged with the portion of the blood collection container. The sleeve further includes a lateral portion, which can include the other end of the sleeve, supports, and/or a collar, that provides support for the hollow conduit. The hollow conduit and the longitudinal portions of the sleeve are configured and arranged to engage with the blood collection container and a blood collection container, and to provide sufficient negative pressure while engaged to pull a predetermined amount of plasma or serum from the blood collection container. The hollow conduit, which can include a double pointed hollow needle, can be coupled to the sleeve and has a first end and a second end. In specific embodiments, the first end of the hollow conduit is configured to pierce an upper portion (e.g., a top) of the blood collection container and to contact a portion of a blood sample contained within the blood collection container. The second end of the hollow conduit is configured to pierce an upper portion (e.g., a top) of a blood transfer container having negative pressure inside that is sufficient to pull a predetermined amount of plasma or serum from the blood collection container. Although embodiments are not so limited, and in some embodiments, the second end of the hollow conduit otherwise engages the blood transfer container which has a pressure-adjusting mechanism, as further described herein.

The hollow conduit can be enclosed by the sleeve-puncturing assembly, in some embodiments. For example, the sleeve has longitudinal portions (e.g., walls) extending from the other end to the open end. The hollow conduit can extend through the other end and toward the open end of the sleeve. The longitudinal portions (e.g., walls) extend past the first end of the hollow conduit, such that the first end of the hollow conduit is contained or otherwise enclosed within a hollow portion (e.g., the interior space) of the sleeve. The sleeve-puncturing assembly can also include a collar that is affixed to the other end of the sleeve on an exterior surface. The collar is hollow and shaped sufficiently for the blood transfer container to be inserted inside the collar. Further, the second end of the hollow conduit can extend through the other end of the sleeve and within the hollow collar. The collar can extend a greater distance from the other end of the sleeve than the second end of the hollow conduit. The collar can thereby contain or otherwise enclose the second end of the hollow conduit, which can mitigate risk of a user contacting the ends.

In a number of embodiments, the open end of the sleeve can have a plurality of protrusions that jut out from the longitudinal portions (e.g., from the walls toward the hollow portion) of the sleeve. The protrusions can be arranged about the circumference of the sleeve and proximal to the open end. The protrusions can flex in response to force exerted in a first direction and resist flexing (e.g., are rigid or less flexible than the other direction) in response to another force exerted in a second direction opposite the first. For example, in response to a force exerted on the protrusions in a direction toward the open end of the sleeve, the protrusions can resist flexing to prevent or mitigate removal of the sleeve-puncturing assembly from the blood collection container.

In another alternative embodiment or as a supplemental feature, embodiments include at least one protrusion situated at the open end of the sleeve. The at least one protrusion is formed as a wedge with a protruding edge angled inward toward the center portion of the sleeve and downward away from the other end of the sleeve (e.g., toward the open end). The at least one protrusion can allow for the sleeve-puncturing assembly to be easily guided over the blood collection container but not as easily removed from the blood collection container due to the wedge tips. In various specific embodiments, the at least one protrusion includes one protrusion that is arranged around the circumference of the open end of the sleeve that can form a tapered open end having the wedge angled inward and downward. In other specific embodiments and or in addition, a plurality of stacked protrusions can be used.

In another embodiment, the sleeve-puncturing assembly includes an additional sleeve having longitudinal portions (e.g., walls) that extend from the other end of the sleeve and in an opposite direction as the open end. The additional sleeve has an additional open end in which the second end of the hollow conduit is enclosed by (e.g., the walls extend to the additional open end and a greater distance than the second end of the hollow conduit extends) and which receives the blood transfer container. Alternatively, and in another embodiment, the sleeve-puncturing assembly includes one sleeve with two open ends. The hollow conduit can be affixed to the longitudinal portions of the sleeve and extend proximally within the sleeve, with both ends being enclosed by the sleeve (e.g., within the hollow portions or space). For example, the hollow conduit is affixed to the sleeve via supports (e.g., beams) that are coupled to one or more of the longitudinal portions of the sleeve on one end and coupled to the hollow conduit on another end. A plurality of supports, which may form a cross shape (e.g., an "X" shape with the hollow conduit in the middle of the "X"), can be used.

In further embodiments, one or more of the first and second ends of the hollow conduit are not enclosed by components of the sleeve-puncturing assembly. For example, the longitudinal portions of the sleeve can extend past the first end of hollow conduit and the sleeve-puncturing assembly may not include the collar. A removable cap (e.g., formed of plastic or other material) can be placed over or otherwise engage the second end of the hollow conduit to enclose the second end, and which is removed prior to coupling or engaging the sleeve-puncturing assembly to the blood transfer container. In another embodiment, the sleeve-puncturing assembly includes the collar, which encloses the second end of the hollow conduit, and the longitudinal portions (e.g., walls) of the sleeve do not extend past the first end of the hollow conduit. A removable cap can be placed over or otherwise engage the first end of the hollow conduit, and which is removed prior to placing the sleeve-puncturing assembly over or engaging with the blood collection container. In another embodiment, the sleeve-puncturing assembly does not include the collar and the longitudinal portions (e.g., walls) of the sleeve do not extend past the first end of the hollow conduit. A first removable cap can be placed over or engage the first end of the hollow conduit and a second removable cap can be placed over or engage the second end of the hollow conduit. The removable caps are removed prior to placing the sleeve-puncturing assembly over or engaging the blood collection container and prior to coupling or engaging the sleeve-puncturing assembly to the blood transfer container.

The upper portions (e.g., tops) of the blood collection container and the blood transfer container can be sealed tops or stoppers formed of rubber or other elastomer material. The upper portions can seal the respective containers, thereby maintaining pressure inside and/or seal of blood inside of the respective container. In some embodiments, the top of the blood transfer container can alternatively include a nozzle, as further described herein.

A blood transfer apparatus, in various embodiments, can include the above-described sleeve-puncturing assembly, and one or more of the blood transfer container and the blood collection container. The blood transfer container has the negative pressure inside that is sufficient to pull a predetermined amount of plasma or serum from the blood collection container (e.g., is a set amount of pressure that pulls the predetermined amount). The negative pressure can also be referred to as vacuum pressure. The blood, as contained in the blood collection container, can have separated layers of cell fraction and plasma or serum. The hollow conduit is a particular length sufficient to contact plasma or serum, but not the cell fraction as contained in the blood collection container. Responsive to placing the sleeve over or engaging the blood collection container, the first end of the hollow conduct pierces the upper portion of the blood collection container and is in contact with the plasma or serum of the blood sample. The blood transfer container can be inserted, placed in contact with, and/or otherwise or engage with the collar which causes the second end of the hollow conduit to pierce the upper portion of the blood transfer container, and the blood transfer container pulls the predetermined amount of the plasma or serum from the blood collection container based on the negative pressure.

In various alternative embodiments, the blood transfer container includes a pressure-adjusting mechanism which is used to generate the negative pressure. For example, the blood transfer container includes a (cylinder) barrel with a plunger or piston on one end and another end for engaging the sleeve-puncturing assembly as described-above. The other end includes the upper portion, such as a nozzle or top (e.g., a sealed top), arranged to engage with the other end of the hollow conduit of the sleeve-puncturing assembly. For example, the nozzle or top is sized to be inserted over the second end of the hollow conduit or into the collar of the sleeve-puncturing assembly. Once the blood transfer container is engaged with the sleeve-puncturing assembly or prior to, a user (or automated arm) pulls the plunger or piston in a direction away from the nozzle or top of the barrel and which generates the negative pressure inside the blood transfer container. The user can change the amount of negative pressure, and the corresponding amount of plasma or serum drawn, on-the-fly and/or during sample collection. The negative pressure, similar to other embodiments, is sufficient to pull the predetermined amount of plasma or serum into the blood transfer container.

Various embodiments are directed to methods of using the sleeve-puncturing assembly and/or a blood transfer apparatus to transfer and/or store blood. The method can include collecting a blood sample in a blood collection container having a sealed upper portion and separating cell fraction from plasma or serum of the blood sample, such as by centrifuging the blood sample in the blood collection container. The method further includes placing a sleeve-puncturing assembly over or otherwise engaging the sleeve-puncturing assembly with the blood collection container, thereby piercing the sealed upper portion of the blood collection container with a first end of a hollow conduit and contacting the plasma or serum with the first end of the hollow conduit. The collar of the sleeve-puncturing assembly engages (e.g., is connected to) a blood transfer container while the first end of the hollow conduit is in contact with the plasma or serum, the blood transfer container having another sealed upper portion that seals a negative pressure inside which is sufficient to pull a predetermined amount of plasma or serum from the blood collection container. In response to the collar engaging the blood transfer container, the method further includes piercing the other sealed upper portion of the blood transfer container with the second end of the hollow conduit and pulling the predetermined amount of plasma or serum into the blood transfer container from the blood collection container via the negative pressure. In accordance with various embodiments, a user and/or an automated arm (e.g., robotics) can be used to place the various components.

The transfer of blood from the blood collection container to the blood transfer container using a sleeve-puncturing assembly can mitigate contamination risk to a user and/or surrounding area. For example, the transfer of plasma/serum can be from a closed system (e.g., blood collection container) to a closed system (e.g., blood transfer container) and can avoid spray of micro-droplets of blood, serum, plasma and/or macro spillage of blood. In some embodiments, as the amount of blood pulled is predetermined and occurs automatically in response to contact between the component of the blood sample, the hollow conduit, and the negative pressure of the blood transfer container, a user does not manually measure the blood and/or use special skills to transfer the blood.

As used herein, the upper portions of the blood collection container and the blood transfer container are herein sometimes interchangeably referred to (and interchangeably include) as "tops" of the containers. The longitudinal portions are sometimes interchangeably referred to (and interchangeably include) as "walls" of the sleeve. In a number of embodiments, the lateral portion of the sleeve includes one or more of the other end of the sleeve, the collar of the sleeve, and the supports, and is sometimes interchangeably referred to (and interchangeably includes) as one or more of "the other end of the sleeve, the collar of the sleeve, and the supports" of the sleeve. As may be appreciated, and as illustrated by FIGS. 2A-2F, the sleeve includes a three-dimensional structure, such as a cylinder-shaped barrel that is hollow and has the open end and the other end. The sleeve, including the longitudinal portions (e.g., the walls) can be formed by a single continuous structure or multiple portions integrated together to form a single structure. The longitudinal portions or walls can be a continuous portion of material, in some embodiments.

Turning now to the figures, FIG. 1A illustrates a sleeve-puncturing assembly in accordance with various embodiments of the present disclosure. In various embodiments, the sleeve-puncturing assembly 100 includes a sleeve 102 and hollow conduit 104. The sleeve 102 has an open end 105 and another end 107, which can be an at least partially closed end such that the sleeve 102 forms a shroud, e.g., is hollow. The sleeve 102 has longitudinal portions, herein referred to as walls, which are configured and arranged to be placed over a blood collection container, such as the blood collection container 114 illustrated to the right of the dashed-line. The open end 105 of the sleeve 102, when the sleeve 102 is placed or being placed over the blood collection container 114, engages with a portion of the blood collection container 114 (e.g., the top 116 or a portion of the tube). When the sleeve 102 is placed over or engages with the blood collection container 114, the blood collection container 114 extends toward the other end 107 of the sleeve 102 and within an interior space of the sleeve 102.

As illustrated, in a first embodiment, the sleeve 102 is a cylindrical barrel having an open end 105 for receiving a blood collection container 114 and the other end 107 for receiving a blood transfer container 110. For example, the open end 105 is configured and arranged to engage with a portion of the blood collection container 114, such as the upper portion (e.g., top 116) of the blood collection container 114. The other end 107 is configured and arranged to provide containment of the blood collection container 114 while the open end 105 is engaged with the portion of the blood collection container 114. The other end 107 can be at least partially closed or can be open in various embodiments. However, and as further illustrated herein, embodiments are not so limited. The sleeve 102 can be formed of a variety of materials including glass, plastic, metal, and other materials. FIG. 1A illustrates a specific embodiment, and embodiments can include other assembly arrangements as further described herein. As further described herein, the sleeve 102 further includes a lateral portion to provide support to the hollow conduit 104. The lateral portion can include the other end 107, a collar 106, supports (e.g., supports 921 illustrated by FIGS. 9A-9B), and various combinations thereof.

The blood collection container 114 can contain a blood sample, e.g., the separated plasma or serum 117 and cell fraction 119. The blood collection container 114 (as well as the blood transfer container 110, in some embodiments, as further described herein) has an upper portion, herein referred to as a "top" 116, that seals the blood sample inside the container, such as a sealed stopper formed of rubber or other types of elastomers that maintains seal of the container, and below (or above depending on the orientation of the container) the top 116 is a chamber for receiving or holding blood. As may be appreciated by one of ordinary skill, the blood collection container 114 can include a vacuum blood tube.

The hollow conduit 104 is supported by, and optionally coupled to, the sleeve 102 and extends proximally within the sleeve 102 toward the open end 105. For example, the hollow conduit 104 can be permanently affixed to the sleeve, such as via other end 107, the walls, and/or the collar 106, and once affixed, may not be removed or otherwise retracted. The hollow conduit 104 and the walls of the sleeve are configured and arranged to engage with the blood collection container 114 and a blood transfer container 110, and to provide sufficient negative pressure while engaged to pull a predetermined amount of plasma or serum from the blood collection container 114 into the blood transfer container 110.

In specific embodiments, the hollow conduit 104 extends past the other end 107 of the sleeve 102, such as through an opening in the other end 107. The hollow conduit 104 has a first end 108 and a second end 109 (which is hidden by the collar 106). The hollow conduit 104 can include a double pointed needle having a gauge of between 7-31, although embodiments are not so limited. Each end 108, 109 of the hollow conduit 104 is sufficiently sharp and/or pointed and configured to pierce tops of blood containers. For example, the first end 108 of the hollow conduit 104 is configured to pierce the top 116 of the blood collection container 114 and to contact a component (e.g., the plasma or serum 117) of the blood sample contained within the blood collection container 114. The first end 108 of the hollow conduit 104 extends into the hollow space (e.g., the interior space) of the blood collection container 114 a sufficient distance to contact the plasma or serum 117 of the blood sample and/or to not extend or otherwise contact the cell fraction 119 of the blood sample. The sufficient distance depends on the size of the blood collection container. For example, the hollow conduit 104, used for a 10 ml blood collection container, can have a length of 2.95 inches from the top of the collar 106 (as further described herein) of the sleeve-puncturing assembly 100 to the first end 108 of the hollow conduit 104. The second end 109 of the hollow conduit 104 is configured to pierce a top of a blood transfer container 110 having negative pressure inside that is sufficient to pull a predetermined amount of plasma or serum 117 from the blood collection container 114. The hollow conduit 104 can extend through the other end 107 of the sleeve 102 and the open end 105 of the sleeve 102 extends past the first end 108 of the hollow conduit 104, as further described below. Similarly to the sleeve 102, the hollow conduit 104 can be formed of a variety of material including metal, plastic, glass, and other materials.

The hollow conduit 104 is enclosed by the sleeve 102 of the sleeve-puncturing assembly 100, in accordance with a number of embodiments. By enclosing the hollow conduit 104, a user that is operating the sleeve-puncturing assembly 100 (and/or operating an automatic arm) to transfer blood to the blood transfer container 110 can have a mitigated risk of being pricked or otherwise contacting the hollow conduit 104 and which may result in contamination of the blood sample collected. The first end 108 of the hollow conduit 104 is enclosed by the walls of the sleeve 102. The walls of the sleeve 102 extend from the open end 105 to the other end 107, and the hollow conduit 104 extends toward the open end 105 of the sleeve 102. The walls extend past the first end 108 so that the sleeve 102 contains the first end 108 of the hollow conduit 104. The second end 109 of the hollow conduit 104 can be enclosed by a collar 106 affixed to the other end 107 of the sleeve 102. The collar 106 is hollow and shaped to engage the blood transfer container 110. In specific embodiments, the collar 106 can connect to the blood transfer container 110, such as a user or automated arm inserting the blood transfer container 110 into the collar 106. For example, the blood transfer container 110 has a top 112 that seals the negative pressure inside the blood transfer container 110, although embodiments are not so limited. The collar is sufficiently shaped so that the top 112 of the blood transfer container 110 can be inserted into the collar 106. As a specific example, if the top 112 is circular, the collar 106 can be circular shaped and having dimensions such that the top 112 of the blood transfer container 110 can be inserted inside the collar 106. The collar 106 can extend past the second end 109 of the hollow conduit 104 (e.g., can extend a greater distance than the second end 109), with the second end 109 of the hollow conduit 104 being contained within the collar 106.

As previously described, the blood transfer container 110 can have a top 112 that maintains a negative pressure (e.g., vacuum pressure) inside the blood transfer container 110. The negative pressure is sufficient to pull a predetermined amount of plasma or serum. In some embodiments, once the negative pressure is set, the blood transfer container 110 as depicted in FIG. 1A may be without any pressure-adjusting mechanism, outside of removing or puncturing the top 112 of the blood transfer container 110 sufficient to expose the blood transfer container 110 to atmospheric pressure or other pressures.

In other embodiments, the blood transfer container 110 includes a pressure-adjusting mechanism which is used to generate the negative pressure. For example, the blood transfer container 110 includes a (cylinder) barrel with a plunger or piston on one end (distal to the end having the top 112) and another end (e.g., proximal to the top 112 illustrated by FIG. 1A) for engaging the sleeve-puncturing assembly 100, as described-above. The other end includes a nozzle or top 112 (e.g., a sealed top) arranged to engage with the second end 109 of the hollow conduit 104 of the sleeve-puncturing assembly 100. For example, the nozzle or top 112 is sized to be inserted over the second end 109 of the hollow conduit 104 or into the collar 106 of the sleeve-puncturing assembly 100. Once the blood transfer container 110 engages the sleeve-puncturing assembly 100 or prior to, a user (or automated arm) pulls the plunger or piston in a direction away from the nozzle or top 112 and which generates the negative pressure inside the blood transfer container 110. The user can change the amount of negative pressure, and the corresponding amount of plasma or serum drawn, on-the-fly and/or during sample collection. For example, the amount of negative pressure inside the blood transfer container 110 and the resulting amount of plasma or blood drawn is based on how far the user (or automated arm) pulls the plunger or piston. The barrel of the blood transfer container 110 can include visual markings to indicate the amount of plasma or blood drawn. Further, the nozzle or top 112 can be configured to contain the plasma or blood drawn inside the barrel once drawn. In specific embodiments, the blood transfer container 110 can include a syringe (without a needle) having the plunger on the one end and the nozzle (or top 112) on the other end configured for engaging the hollow conduit 104, although embodiments are not so limited and can include other types of blood transfer container having pressure-adjusting mechanisms.

The sleeve-puncturing assembly 100 engages with or couples to the blood transfer container 110 having the negative pressure, as further illustrated by FIG. 1B. In response (and while the first end 108 of the hollow conduit 104 is in contact with the component of the blood sample), the second end 109 of the hollow conduit 104 pierces the sealed top 112 of the blood transfer container 110 in order to apply the negative pressure on the plasma or serum 117 and pulls the plasma or serum 117 into the blood transfer container 110 from the blood collection container 114. The amount of plasma or serum drawn is predetermined based on the negative pressure and which can depend on the length that he hollow conduit 104 extends into the blood collection container 114. For example, the hollow conduit 104 is a sufficient length that the first end 108 of the hollow conduit 104 contacts the plasma or serum 117 in order to apply the negative pressure on the plasma or serum 117. The sealed top 112 can include a rubber or other type of elastomer that maintains the seal of the blood transfer container 110, thereby maintaining the negative pressure inside the blood transfer container 110 and also maintaining the plasma or serum pulled in.

As further illustrated and described in connection with FIG. 1B, the sleeve 102 is placed over the blood collection container 114 resulting in the first end 108 of the hollow conduct piercing the top 116 of the blood collection container 114 and the first end 108 being in contact with the plasma or serum 117 of the blood sample. The blood transfer container 110 engages the collar 106 (e.g., placed in contact with the collar 106), resulting in the second end 109 of the hollow conduit 104 piercing the top 112 of the blood transfer container 110, and the blood transfer container 110 pulling the predetermined amount of the plasma or serum 117 from the blood collection container 114 based on the negative pressure inside.

In various embodiments, a blood transfer apparatus can include one or more of the components illustrated by FIG. 1A. For example, an apparatus can include the sleeve-puncturing assembly 100 and the blood transfer container 110. Other apparatus embodiments include the sleeve-puncturing assembly 100 and the blood collection container 114. Further apparatus embodiments include the sleeve-puncturing assembly 100, the blood transfer container 110, and the blood collection container 114. Additionally, although the blood sample is illustrated as having the plasma or serum 117 separated from the cell fraction 119, embodiments are not so limited. In some embodiments, a blood sample is not separated and the blood is centrifuged to separate the plasma or serum. As may be appreciated, the blood sample can be collected from an organism and/or can be already collected and stored.

The blood collection container 114 and the blood transfer container 110, as would be appreciated by one of ordinary skill, have a chamber below or above the tops 112, 116 for containing a blood sample. The tops 112, 116 can be self-sealing after the hollow conduit 104 pierces the respective tops and is removed.

In various related-embodiments, as further illustrated and described in connection with FIGS. 2A-2B, the sleeve 102 further includes a plurality of protrusions. The protrusions can be arranged about the circumference of the sleeve 102 proximal to the open end 105. For example, the protrusions are affixed to the longitudinal portions (e.g., the walls) of the sleeve 102, proximal to the open end 105, and jut out from the interior surface toward the center portion of the sleeve 102 (e.g., center of the circumference of the sleeve 102). The protrusions can prevent and/or mitigate removal of the sleeve-puncturing assembly 100 from the blood collection container 114 via engagement of the protrusions with the top 116 of the blood collection container 114, as further described herein.

In specific embodiments, the illustrated sleeve-puncturing assembly 100 can include one or more removable caps. For example, one or more of the first end 108 and the second end 109 of the hollow conduit 104 can be additionally (or alternatively) enclosed by a removable cap. The removable caps can be cup-shaped and can engage the other end 107 of the sleeve 102 (proximal to an interior surface and exterior surface of the sleeve 102, respectively), such as via frictional engagement. A removable cap can be placed over the first end 108 of the hollow conduit 104 and engage the other end 107 of the sleeve 102 proximal to an interior surface of the sleeve 102, and can be removed prior to placing the sleeve-puncturing assembly 100 over the blood collection container 114. A (or another) removable cap can be placed over the second end 109 of the hollow conduit 104 and engage with the other end 107 of the sleeve 102 proximal to an exterior surface of the sleeve 102, and can be removed prior to engaging or coupling the sleeve-puncturing assembly 100 with the blood transfer container 110.

In another alternative embodiment or as a supplemental feature, embodiments include at least one protrusion situated at the open end 105 of the sleeve 102. The at least one protrusion is formed as a wedge with a protruding edge angled inward toward the center portion of the sleeve 102 and downward away from the other end 107 of the sleeve 102 (e.g., toward the open end 105). For example, the at least one protrusion generates a taper at the open end 105 of the sleeve 102 proximal to the hollow space of the sleeve 102 (e.g., internal surface or space formed by the walls). The at least one protrusion can allow for the sleeve-puncturing assembly 100 to be easily guided over the blood collection container 114 but not as easily removed from the blood collection container 114 due to the wedge tips. In various specific embodiments, the protrusion is arranged around the circumference of the open end 105 (e.g., on the walls) of the sleeve 102 and forms the tapered open end 105 having the wedge (e.g., a lip) angled inward and downward. In other specific embodiments and or in addition, a plurality of stacked protrusions can be used.

FIG. 1B illustrates an example method for transferring blood from a blood collection container to a blood transfer container, in accordance with various embodiments of the present disclosure. In various embodiments, a blood transfer apparatus is used to perform the illustrated method. The blood transfer apparatus includes the sleeve-puncturing assembly 100 and, optionally, one or more of the blood collection container 114 and the blood transfer container 110, as illustrated by FIG. 1A in various embodiments. As illustrated by FIG. 1B, at 120, a sample of blood 122 is collected or otherwise located in a blood collection container 114 having a sealed top 116. At 124, cell fraction 119 is separated from the plasma or serum 117. For example, the blood sample 122, as illustrated at 120, can be centrifuged to separate cell fraction from plasma or serum, as illustrated by the separated cell fraction 119 (e.g., red blood cells, bottom of the container) and the plasma or serum 117 (top of the container). In specific embodiments, when using plasma and as would be appreciated by one of ordinary skill in the art, the blood collection container 114 can contain anticoagulants, and after collecting the blood, is centrifuged to separate the blood cells from the serum. At the end of the centrifugation step, the red blood cells are at the bottom of the blood collection container 114, and the serum or plasma is at the top. A separating gel can be at the interface between the blood cells and the serum or plasma. For example, the separating gel adheres to the interior wall of the blood collection container 114 so that when the blood collection container 114 is inverted, the gel does not move with respect to the blood collection container 114.

As would be appreciated by one of ordinary skill, plasma can include a liquid and cell-free portion of blood that has been prevented from clotting (e.g., serum with clotting factor). Serum can include a liquid and cell-free portion of blood after it has been allowed to clot (e.g., plasma without clotting factor, such as fibrinogen). And, cell fraction can include red blood cells and buffy coat (e.g., white blood cells mixed with platelets).

The blood collection container 114, having a blood sample with separated plasma and/or serum 117, can optionally be placed in a container holder 128 for stability and handling. Although embodiments are not so limited, and in some instances, the blood collection container 114 is held by the user, an automated arm, and/or other devices.

At 126, the sleeve-puncturing assembly 100 is placed over or engages the blood collection container 114, such as the sleeve-puncturing assembly 100 previously described and illustrated with regards to FIG. 1A. Placing the sleeve-puncturing assembly 100 over or engaging the blood collection container 114 can result in the first end of the hollow conduit 104 of the sleeve-puncturing assembly 100 piercing the sealed top 116 of the blood collection container 114 and contacting the plasma or serum 117. For example, the sleeve of the sleeve-puncturing assembly 100 is placed over the blood collection container 114 which results in the first end of the hollow conduit 104 inserting inside the blood collection container 114 and contacting the plasma or serum 117. The first end of the hollow conduit 104, as illustrated, extends a distance sufficient to clear the top 116 of the blood collection container 114 and to contact the plasma or serum 117, but does not contact the cell fraction 119 of the blood sample.

While contacting the component of the blood sample with the first end of the hollow conduit 104 of the sleeve-puncturing assembly 100, at 130, the collar 106 of the sleeve-puncturing assembly 100 is engaged with (or coupled to) the blood transfer container 110. For example, the blood transfer container 110 can be inserted into the collar 106 via the top 112 of the blood transfer container 110 such that the collar 106 is connected to the blood transfer container 110. As previous described, the blood transfer container 110 has another sealed top 112 which seals a negative pressure inside the blood transfer container 110. In response to engaging the collar 106 with the blood transfer container 110, the other sealed top 112 is pierced by the second end of the hollow conduit 104 and the predetermined amount of plasma or serum 132 is pulled into the blood transfer container 110 from the blood collection container 114 via the negative pressure. Once the negative pressure is set, the blood transfer container 110 as depicted by FIG. 1B may be without any pressure-adjusting mechanism, outside of removing or puncturing the top of the blood transfer container sufficient to expose the blood transfer container to atmospheric pressure or other pressures. In other embodiments, the blood transfer container 110 includes a pressure-adjusting mechanism which is used to generate the negative pressure, such as a plunger as previously described.

As may be appreciated, method embodiments in accordance with the present disclosure are not limited to methods that include each of the steps illustrated by FIG. 1B. For example, the blood sample may have been previously obtained and stored. In other embodiments, the blood sample may have been previously centrifuged and stored. Accordingly, method embodiments can include subsets or all of the illustrated steps.

Figure 2A:
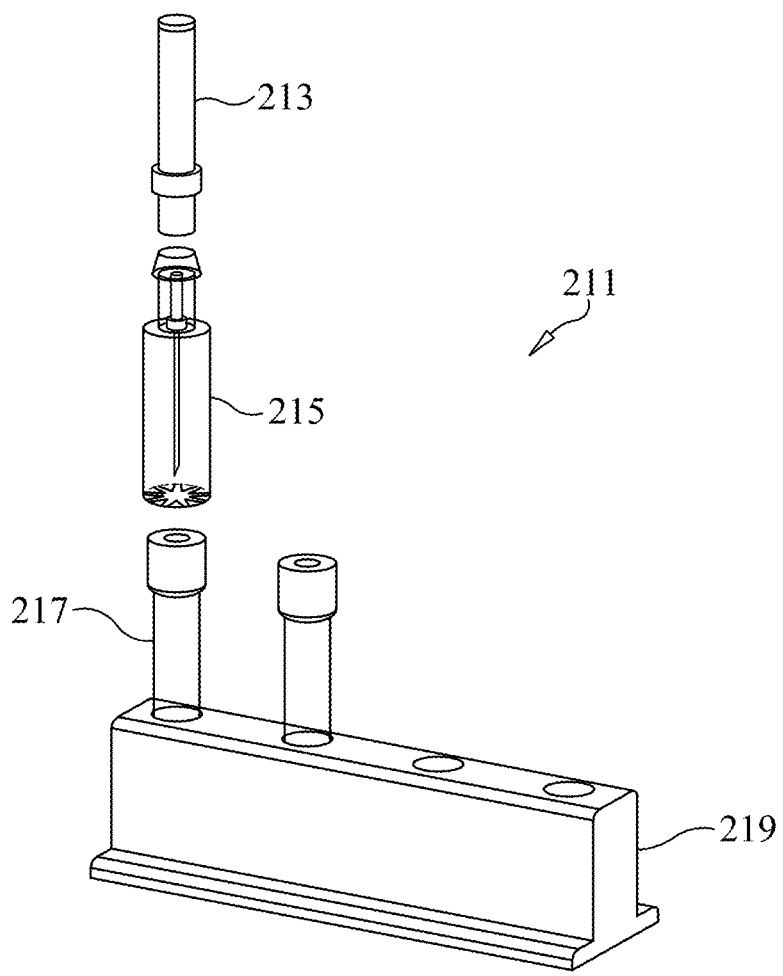
FIGS. 2A-2F illustrate examples of a blood transfer apparatus in accordance with various embodiments of the present disclosure.
Figure 2B:
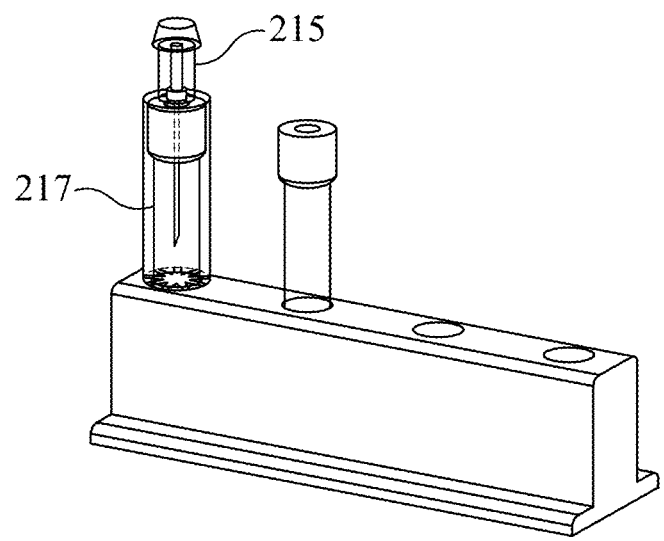

FIGS. 2A-2F illustrate examples of a blood transfer apparatus in accordance with various embodiments of the present disclosure. The blood transfer apparatus illustrated by FIGS. 2A-2F can include the blood transfer apparatus illustrated by FIG. 1A, although embodiments are not so limited. FIG. 2A illustrates a blood transfer apparatus 211 that includes a blood transfer container 213, a sleeve-puncturing assembly 215, and a blood collection container 217, and, optionally, a container holder 219, although embodiments are not limited to apparatuses that include each of the illustrated components. More specifically, FIG. 2A illustrates an example sleeve-puncturing assembly 215 prior to placement over the blood collection container 217 and prior to engaging, such as via insertion, the blood transfer container 213. FIG. 2B illustrates the sleeve-puncturing assembly 215 as placed over the blood collection container 217.

Figure 2C:
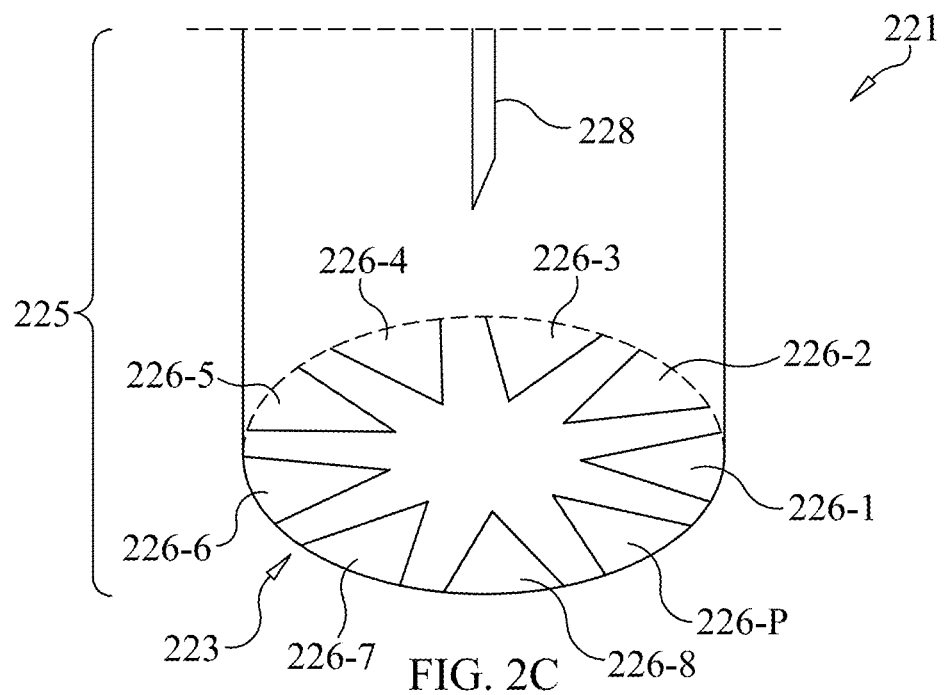
Figure 2D:
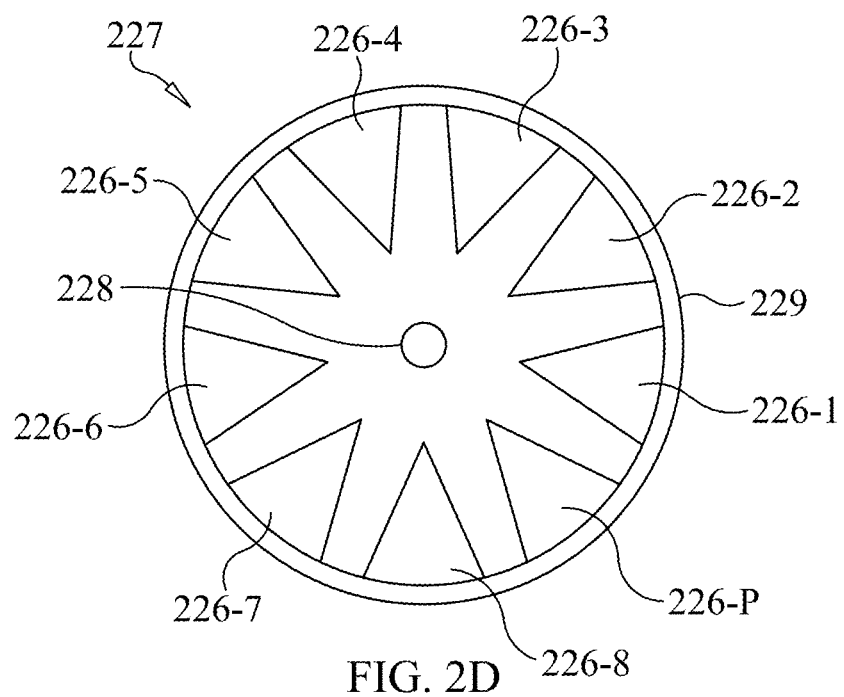

In accordance with various embodiments, the sleeve-puncturing assembly 215 includes a plurality of protrusions. For example, as illustrated by FIGS. 2C and 2D, the open end of the sleeve has a plurality of protrusions that jut out from the walls towards a center portion of the sleeve (e.g., toward a hollow portion of the sleeve, such as an interior surface or space) of the sleeve proximal to the open end. The protrusions can extend from the walls of the sleeve toward the center portion of the sleeve. FIG. 2C illustrates a side-view 221 of the open end 223 of the sleeve 225 having the protrusions 226-1, 226-2, 226-3, 226-4, 226-5, 226-6, 226-7, 226-8 . . . 226-P (herein referred to as "protrusions 226" for ease of reference) arranged about the circumference of the sleeve 225. FIG. 2D illustrates a bottom view 227 of the open end of the sleeve having the protrusions 226 arranged about the circumference 229 of the sleeve (and which extend from the walls of the sleeve). The views of the open end of the sleeve illustrated by FIGS. 2C-2D can include partial views of the sleeve-puncturing assembly, and illustrate the first end of the hollow conduit 228 enclosed by the sleeve 225. Although the embodiment of FIG. 2C-2D illustrates a plurality of protrusions, embodiments are not so limited and can include or additionally include a single protrusion (or more) situated at the open end of the sleeve that is formed as a wedge with a protruding edge angled inward toward the center portion of the sleeve and downward away from the other end of the sleeve (e.g., toward the open end), and/or a plurality of stacked protrusions can be used, as previously described.

The protrusions 226 can include (triangular-shaped or cone-shaped) teeth that are arranged about the circumference 229 of the sleeve proximal to the open end, and, in more-specific embodiments, are uniformly spaced about the circumference 229.

However, embodiments are not so limited and the protrusions 226 can be a variety of shapes, such as wedges, and can be non-uniformly spaced. The protrusions 226 can be formed of a variety of material such as plastic, rubber, and other elastomers. In various embodiments, the protrusions 226 are formed of two or more different materials to provide flexing of different levels responsive to forces in the different directions. The protrusions 226 can flex in response to a force exerted thereon in a first direction and resist flexing (e.g., rigid or less flexible than the first direction) in response to another force exerted thereon in a second direction opposite the first direction. For example, responsive to a force exerted on the protrusions 226 in a direction toward the other end of the sleeve 225, the protrusions flex. In response to a force exerted on the protrusions 226 in a direction toward the open end 223 of the sleeve 225, the protrusions resist flexing.

Figure 2E:
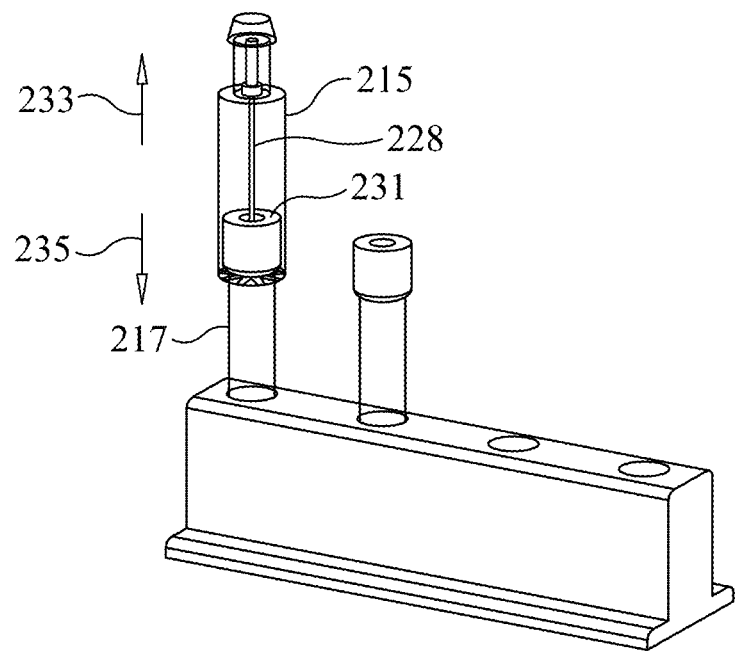

FIG. 2E illustrates an example of the protrusions resisting a force exerted thereon in a particular direction. When the sleeve-puncturing assembly 215 is placed on or engages the blood collection container 217, a force is exerted on the protrusions in a direction 233 toward the other end of the sleeve. In response to the force, the protrusions flex to allow the sleeve-puncturing assembly 215 to pass over the top 231 of the blood collection container 217. If the user or automated arm attempts to remove the sleeve-puncturing assembly 215 from the blood collection container 217, as illustrated by FIG. 2E, a force is exerted on the protrusions in a direction 235 toward the open end. The protrusions may not flex or resist flexing and can prevent or mitigate removal of the sleeve-puncturing assembly 215 from the blood collection container 217. As illustrated by FIG. 2E, the top 231 of the blood collection container has a greater diameter and/or circumference than a diameter and/or circumference of blood collection container 217 such that the protrusions can engage with the top 231 of the blood collection container 217 to prevent or mitigate removal of the sleeve-puncturing assembly 215 from the blood collection container 217. More specifically, the top 231 of the blood collection container 217, which has a greater diameter than the blood collection container 217, provides a ledge which engages the protrusions when a user (and/or automated arm) attempts to remove the sleeve-puncturing assembly 215 from the blood collection container 217. The protrusions are effectively caught by the ledge and can prevent or mitigate further movement of the sleeve-puncturing assembly 215 in a direction 233 toward the top 231 of the blood collection container 217. The protrusions preventing or mitigating removal of the sleeve-puncturing assembly 215 can prevent a user from removing and/or can avoid accidental removal of the sleeve-puncturing assembly 215, which can result in the user contacting the hollow conduit 228 therein.

Figure 2F:
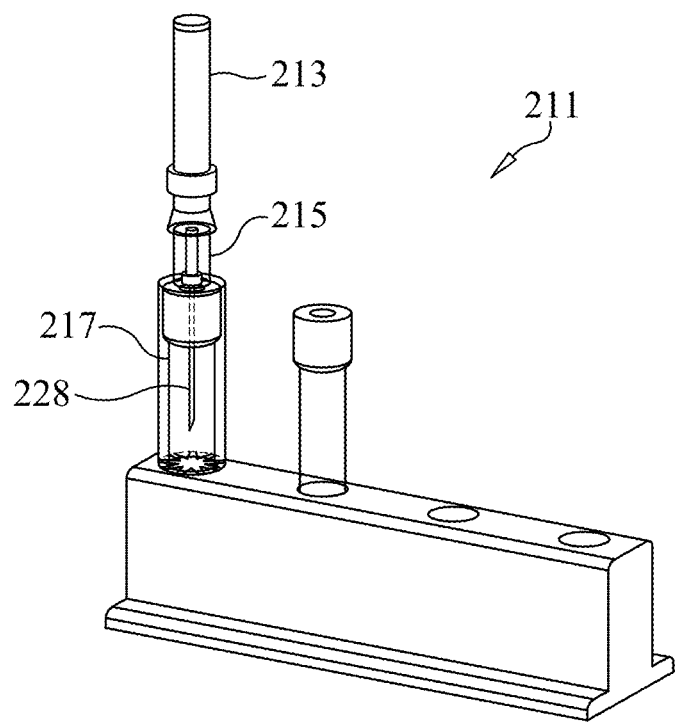

FIG. 2F illustrates the sleeve-puncturing assembly 215 as placed over the blood collection container 217 and with the blood transfer container 213 engaged (e.g., coupled to and/or inserted). As previously described, the blood transfer container 213 can be preloaded with vacuum, which is also referred to herein as "a set amount of negative pressure" or "sufficient negative pressure" to aspirate a specific fixed volume of plasma or serum from the blood collection container 217. By preloading the blood transfer container 213 with a set amount of negative pressure, the user that transfers (e.g., on their own or via an automated arm) the blood may not use any special skill to aspirate the blood sample. Although as may be appreciated, embodiments are not so limited and the blood transfer container 213 can include pressure-adjusting mechanisms. Further, as both containers 213, 217 are sealed by tops and the transfer occurs via an enclosed hollow conduit 228 of the sleeve-puncturing assembly 215, there can be a mitigated risk of contamination of the surrounding area or the user from the blood sample and which can otherwise occur when opening the blood collection container top (e.g., stopper/cap). And, as the ends of the hollow conduit 228 used to pierce both containers 213, 217 is enclosed by the sleeve and/or collar of the sleeve-puncturing assembly 215, there can be a mitigated risk to a user of a needle stick as the ends of the hollow conduit 228 are protected. The sleeve-puncturing assembly 215 and/or the entire apparatus can be used for a variety of purposes such as blood transfer and for storage (cold, room temperature, or frozen) of plasma or serum until ready for analysis.

In various embodiments, the amount of plasma or serum pulled into the blood transfer container 213 is dependent on the length that the hollow conduit 228 (e.g., a needle) of the sleeve-puncturing assembly 215 extends into the interior of the blood collection container 217. For example, for a 10 ml blood collection container 217, the hollow conduit 228 can be a length of 2.95 inches (e.g., the length of needle in device, from the top collar to bottom, for 10 ml blood collection tube, assuming average Hematocrit value of 42%).

Figure 3B:
FIGS. 3A-3B illustrates examples of setting a blood transfer container with negative pressure in accordance with various embodiments of the present disclosure.
Figure 3A:
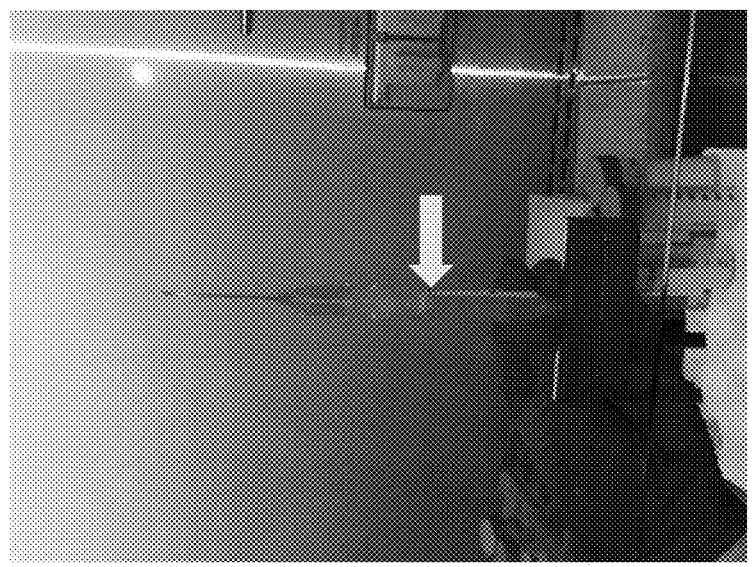

FIGS. 3A-3B illustrates examples of setting a blood transfer container with negative pressure in accordance with various embodiments of the present disclosure. As illustrated by FIG. 3A, the volume of plasma matches the line on the container for 2.7 ml (plus or minus 0.1 ml). FIG. 3B illustrates an example of a blood transfer container that has a preset negative (air) pressure (e.g., 2.7 ml of preloaded vacuum volume). The amount of plasma or serum drawn is a function of the amount of negative pressure, the diameter of the blood transfer container, and the length of the blood transfer container.

Figure 4:
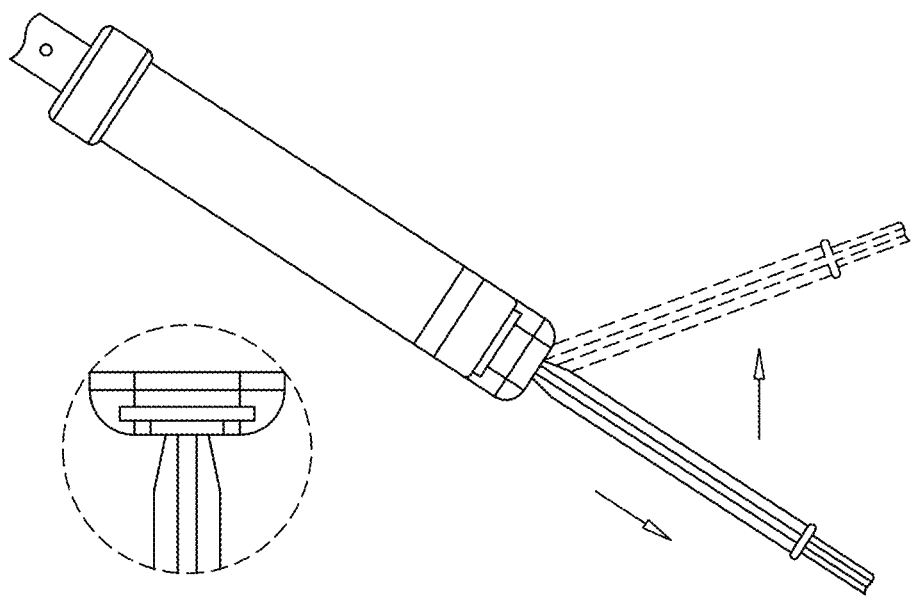
FIG. 4 illustrates an example of a blood transfer container in accordance with various embodiments of the present disclosure.

FIG. 4 illustrates an example of a blood transfer container in accordance with various embodiments of the present disclosure. In various experimental embodiments, the blood transfer container can include a tube with no additive, such as the Sarstedt #05.1729.001 (66×11.5 mm) monovette 2.7 ml volume tube, that fits into the collar of the sleeve-puncturing assembly. This particular tube is designed to have a vacuum generated by the user by pulling the plunger device to maximum and then breaking off the stem as shown. However, embodiments are not so limited and can include other types of containers. As an example, any vacuum tube (with pre-determined volume for specific application) can be used to accomplish the collection of the plasma from the pre-centrifuged blood collection container, such as a generic vacuum style plastic collection tube.

FIGS. 5A-9B illustrate examples of sleeve-puncturing assemblies in accordance with various embodiments. The sleeve-puncturing assemblies illustrated by FIGS. 1A-1B (as well as other figures) can include a first embodiment in which the sleeve-puncturing assembly encloses the hollow conduit via the walls of the sleeve and a collar. However, embodiments are not so limited.

Figure 5B:
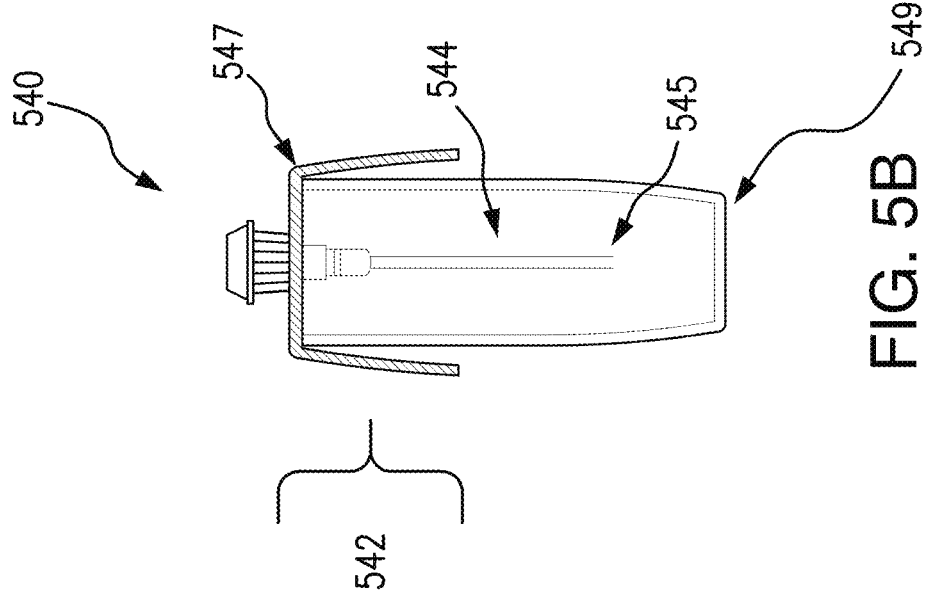
FIGS. 5A-5B illustrate an example of a sleeve-puncturing assembly in accordance with various embodiments.
Figure 5A:
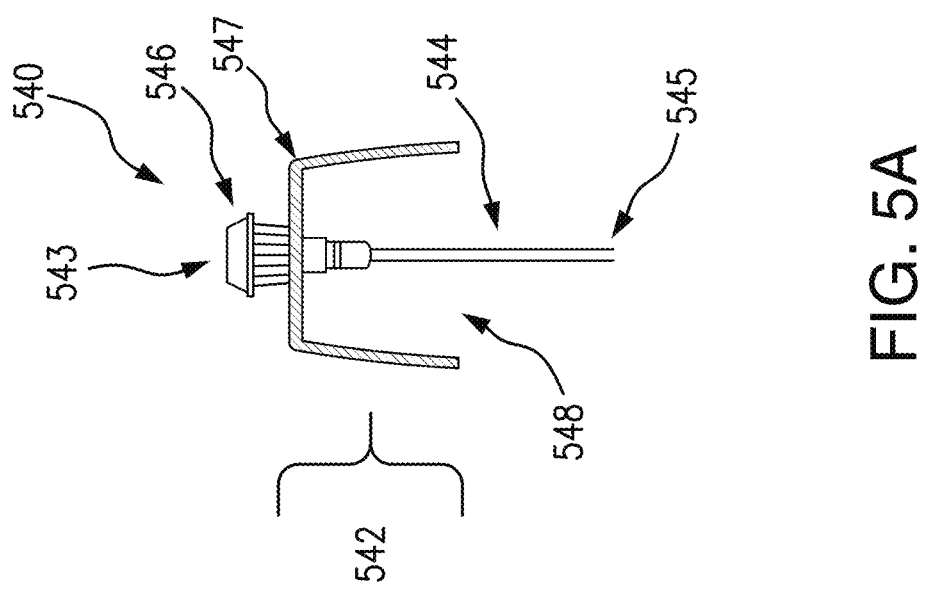

FIGS. 5A-5B illustrate a sleeve-puncturing assembly according to a second embodiment. The sleeve-puncturing assembly 540 includes a sleeve 542 and a hollow conduit 544. The sleeve 542, in the second embodiment, can be a cylindrical barrel having an open end 548 for receiving a blood collection container and another end 547 for receiving a blood transfer container. The hollow conduit 544 is coupled to the sleeve 542 and includes a first end 545 configured to pierce a top of the blood collection container and a second end 543 configured to pierce a top of the blood transfer container. In more-specific embodiments, the hollow conduit 544 is permanently affixed to the other end 547 of the sleeve 542, longitudinal portions (e.g., walls) of the sleeve, and/or an interior surface of the sleeve 652, and once affixed, may not be removed or otherwise retracted. The first end 545 of the hollow conduit 544 can contact plasma or serum of a blood sample contained within the blood collection container. As previously described, the blood transfer container has a negative pressure inside sufficient to pull a predetermined amount of plasma or serum from the blood collection container. The blood collection container and blood transfer container, according to the second embodiment, can be the same containers as previously described and illustrated in FIGS. 1A and 1B.

In the second embodiment, the first end 545 of the hollow conduit 544 is not enclosed by the sleeve-puncturing assembly 540 and the second end 543 of the hollow conduit 544 is enclosed via a collar 546 affixed to the other end 547 of the sleeve 542, as previously described in connection with FIG. 1A. The hollow conduit 544 extends proximally within the sleeve 542 and past the walls of the sleeve 542.

As illustrated by FIG. 5B, the first end 545 of the hollow conduit 544 can be enclosed by a removable cap 549. The removable cap 549 can be cup-shaped and can engage the other end 547 of the sleeve 542 proximal to the hollow portion (e.g., interior surface and/or space) of the sleeve 542, such as via frictional engagement. For example, the removable cap 549 is placed over the first end 545 of the hollow conduit 544 and engages with the other end 547 of the sleeve 542, and the removable cap 549 is removed prior to placing the sleeve-puncturing assembly 540 over or engaging a blood collection container.

Figure 6B:
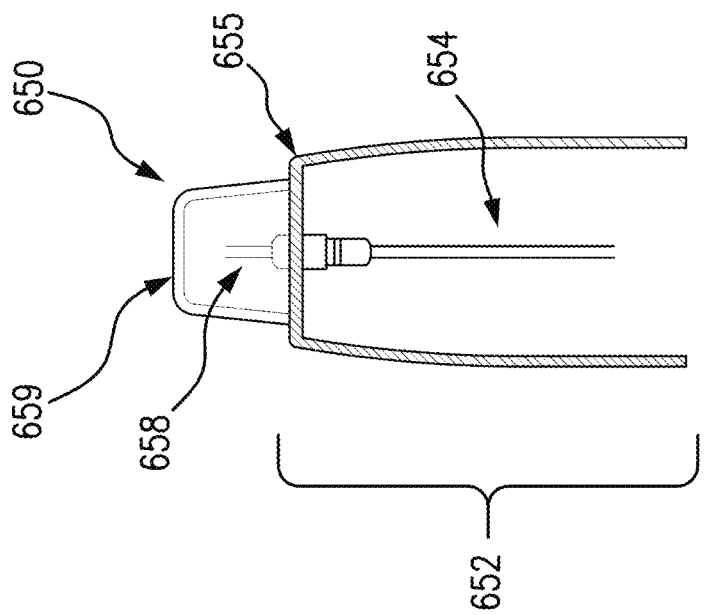
FIGS. 6A-6B illustrate an example of a sleeve-puncturing assembly in accordance with various embodiments.
Figure 6A:
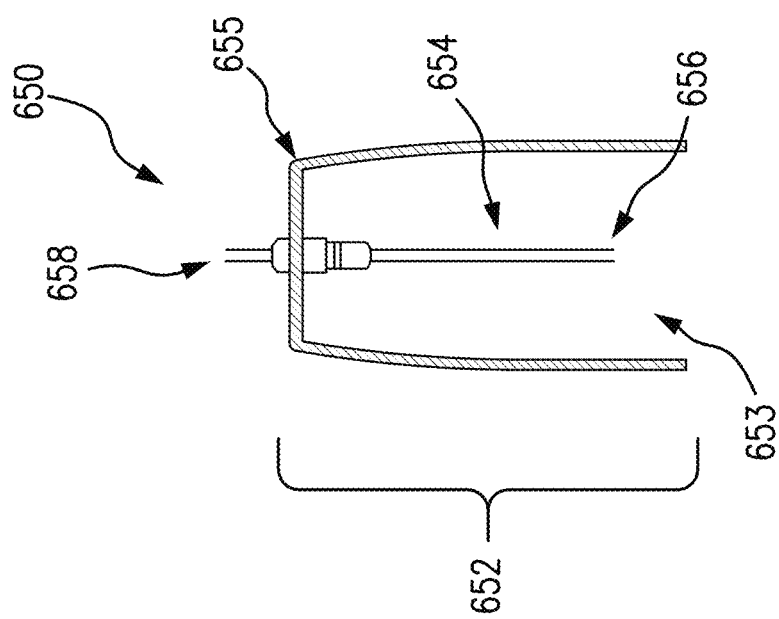

FIG. 6A-6B illustrates a sleeve-puncturing assembly according to a third embodiment. The sleeve-puncturing assembly 650 includes a sleeve 652 and a hollow conduit 654. The sleeve 652, in the third embodiment, can be a cylindrical barrel having an open end 653 for receiving a blood collection container and another end 655 for receiving a blood transfer container. The hollow conduit 654 is coupled to the sleeve 652 and includes a first end 656 configured to pierce a top of the blood collection container and a second end 658 configured to pierce a top of the blood transfer container. In specific embodiments, the hollow conduit 654 is permanently affixed to the other end 655 of the sleeve 652, walls of the sleeve 652, and/or an interior surface of the sleeve 652, and once affixed, may not be removed or otherwise retracted. The first end 656 of the hollow conduit 654 can contact a plasma or serum of a blood sample contained within the blood collection container. As previously described, the blood transfer container has a negative pressure inside sufficient to pull a predetermined amount of plasma or serum from the blood collection container. The blood collection container and blood transfer container, according to the third embodiment, can be the same containers as previously described and illustrated in FIGS. 1A and 1B.

In the third embodiment, the first end 656 of the hollow conduit is enclosed by the sleeve-puncturing assembly 650 and the second end 658 of the hollow conduit 544 is not enclosed. The sleeve-puncturing assembly 650 may not include a collar affixed to the other end 655 of the sleeve 652, as previously described in connection with FIG. 1A. The hollow conduit 654 extends proximally within the sleeve 652 toward the open end 653 and extends past the other end 655 of the sleeve 652 such that the second end 658 of the hollow conduit 654 may be exposed to the surrounding environment.

As illustrated by FIG. 6B, the second end 658 of the hollow conduit 654 can be enclosed by a removable cap 659. The removable cap 659 can be cup-shaped and can engage the other end 655 of the sleeve 652 proximal to an exterior surface of the sleeve 652, such as via frictional engagement. The removable cap 659 can be placed over the second end 658 of the hollow conduit 654 and engage the other end 655 of the sleeve 652, and the removable cap 659 can be removed prior to engaging the sleeve-puncturing assembly 650 with the blood transfer container.

Figure 7B:
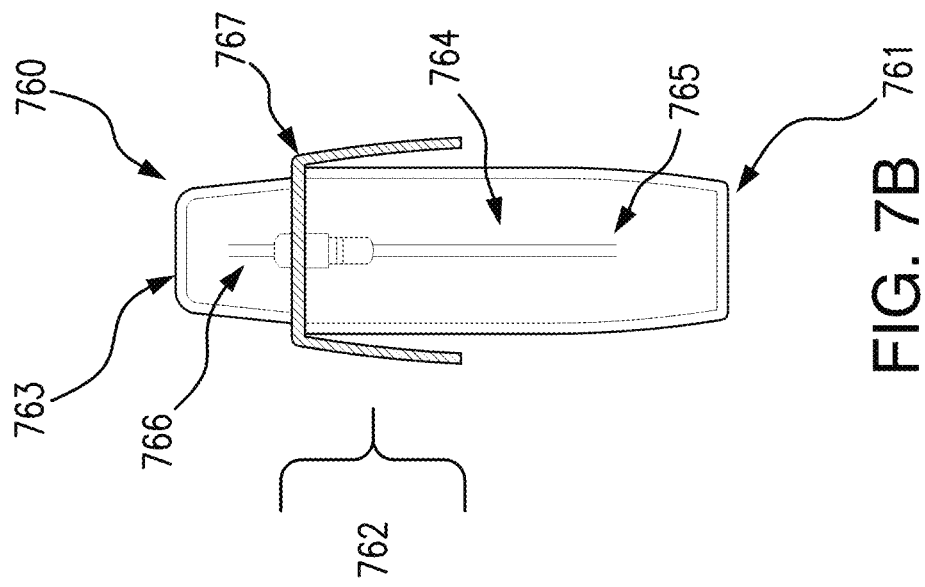
FIGS. 7A-7B illustrate an example of a sleeve-puncturing assembly in accordance with various embodiments.
Figure 7A:
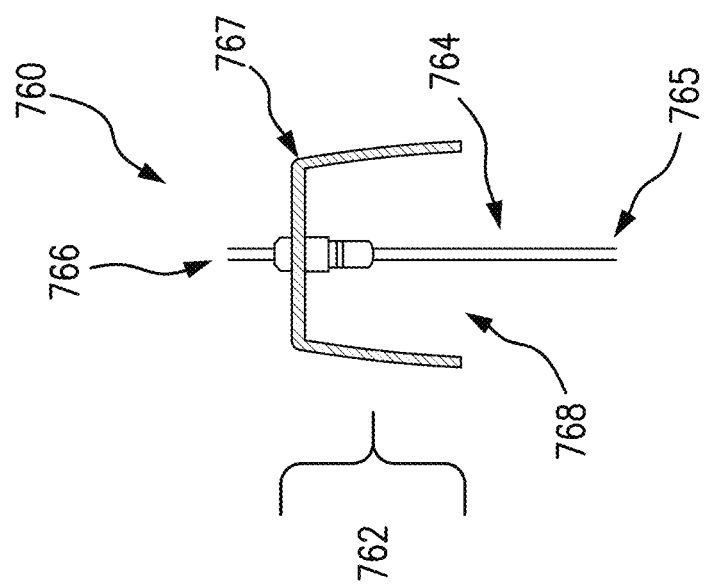

FIG. 7A-7B illustrates a sleeve-puncturing assembly according to a fourth embodiment. The sleeve-puncturing assembly 760 includes a sleeve 762 and a hollow conduit 764. The sleeve 762, in the fourth embodiment, can be a cylindrical barrel having an open end 768 for receiving a blood collection container and another end 767 for receiving a blood transfer container. The hollow conduit 764 is coupled to the sleeve 762 and includes a first end 765 configured to pierce a top of the blood collection container and a second end 766 configured to pierce a top of the blood transfer container. The first end 765 of the hollow conduit 764 can contact plasma or serum of a blood sample contained within the blood collection container. As previously described, the hollow conduit 764 can be permanently affixed to the other end 767 of the sleeve 762, the walls of the sleeve 762, and/or an interior surface of the sleeve 762, and once affixed, may not be removed or otherwise retracted. Further, the blood transfer container has a negative pressure inside sufficient to pull a predetermined amount of plasma or serum from the blood collection container. The blood collection container and blood transfer container, according to the fourth embodiment, can be the same containers as previously described and illustrated in FIGS. 1A and 1B.

In the fourth embodiment, both the first end 765 and the second end 766 of the hollow conduit 764 are not enclosed by the sleeve 762. The sleeve-puncturing assembly 760 may not include a collar affixed to the other end 767 of the sleeve 762, as previously described in connection with FIG. 1A. The hollow conduit 764 extends proximally within the sleeve 762 toward and past the open end 768 and can extend past the other end 767 of the sleeve 762. Accordingly, both the first end 765 and the second end 766 of the hollow conduit 764 can be exposed to the surrounding environment.

As illustrated by FIG. 7B, the first end 765 and the second end 766 of the hollow conduit 764 can be enclosed, respectively, by a first removable cap 761 and a second removable cap 763. The first and second removable caps 761, 763 can be cup-shaped and can engage the other end 767 of the sleeve 762 (proximal to an interior surface and exterior surface of the sleeve 762, respectively), such as via frictional engagement. The first removable cap 761 can be placed over the first end 765 of the hollow conduit 764 and engage the other end 767 of the sleeve 762 proximal to a hollow portion (e.g., an interior or space) of the sleeve 762, and the first removable cap 761 can be removed prior to placing the sleeve-puncturing assembly 760 over or engaging the blood collection container. The second removable cap 763 can be placed over the second end 766 of the hollow conduit 764 and engage with the other end 767 of the sleeve 762 proximal to an exterior surface of the sleeve 762, and the second removable cap 763 can be removed prior to engaging the sleeve-puncturing assembly 760 with the blood transfer container.

Figure 8A:
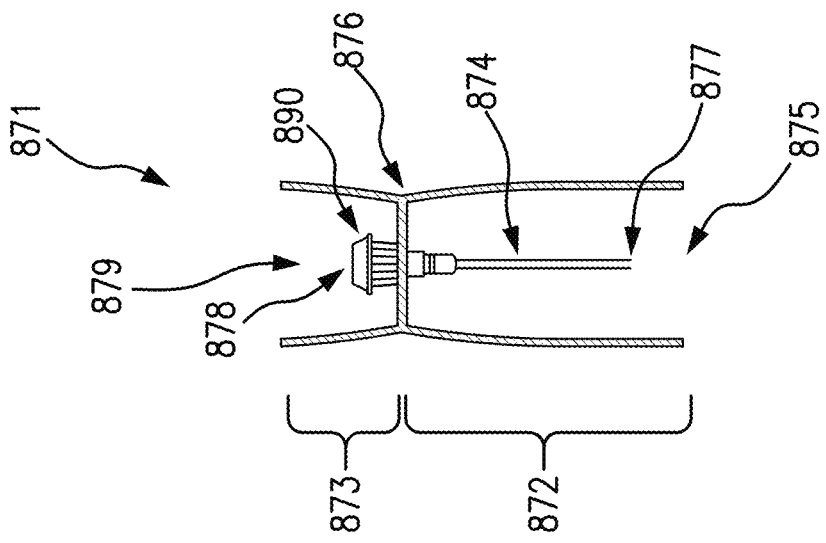
FIGS. 8A-8B illustrate examples of sleeve-puncturing assemblies in accordance with various embodiments.
Figure 8B:
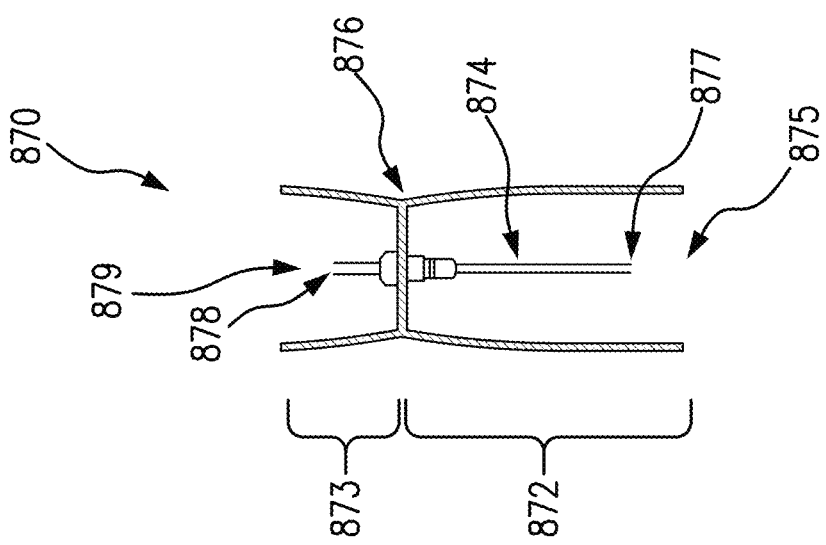

FIGS. 8A-8B illustrates example sleeve-puncturing assemblies according to a fifth embodiment and sixth embodiment. In the fifth and sixth embodiments, the sleeve-puncturing assembly 870, 871 includes a first sleeve 872, a second sleeve 873, and a hollow conduit 874. The first sleeve 872, in the fifth and sixth embodiments, can be a cylindrical barrel having an open end 875 for receiving a blood collection container and another end 876 through which the hollow conduit 874 extends through. The second sleeve 873 can be proximal to the first sleeve 872 such that the first sleeve 872 and second sleeve 873 share the other end 876. The second sleeve 873 can be another cylindrical barrel having an open end 879 for receiving a blood transfer container and the other end 876. The hollow conduit 874 is coupled to at least one of the first and second sleeves 872, 873 and includes a first end 877 configured to pierce a top of the blood collection container and a second end 878 configured to pierce a top of the blood transfer container. For example, the hollow conduit 874 can be permanently affixed to the other end 876 of the sleeves 872,873, the walls of at least one of the sleeves 872, 873, and/or an interior surface of at least one of the sleeves 872,873, and once affixed, may not be removed or otherwise retracted. The first end 877 of the hollow conduit 874 can contact plasma or serum of a blood sample contained within the blood collection container. As previously described, the blood transfer container has a negative pressure inside sufficient to pull a predetermined amount of plasma or serum from the blood collection container. The blood collection container and blood transfer container, according to the fifth and sixth embodiments, can be the same containers as previously described and illustrated in FIGS. 1A and 1B.

In the fifth and six embodiments, the first end 877 and the second end 878 of the hollow conduit 874 are enclosed respectively by the first sleeve 872 and the second sleeve 873. The hollow conduit 874 extends proximally within the first sleeve 872 via the first end 877 and extends proximally within the second sleeve 873 via the second end 878. The walls of the first sleeve 872 extend past the first end 877 of the hollow conduit 874 and the walls of the second sleeve 873 extend past the second end 878 of the hollow conduit. Further, in the six embodiment as depicted by FIG. 8B, the sleeve-puncturing assembly 871 can include a collar 890 that encloses the second end 878 of the hollow conduit 874. The collar 890 is affixed to the other end 876 of the first and second sleeves 872, 873 (e.g., proximal to an exterior surface of the first sleeve 872 and proximal to a hollow portion of the second sleeve 873), as previously described in connection with FIG. 1A, and which can engage or couple to the blood collection container.

Figure 9A:
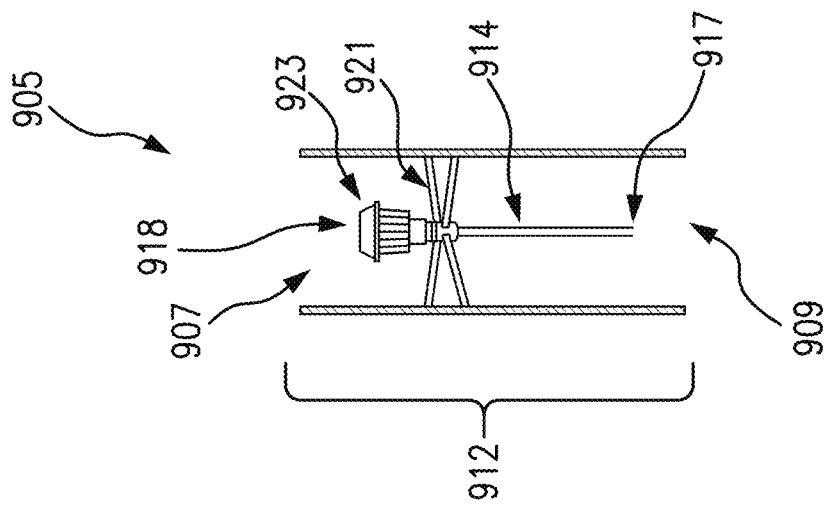
FIGS. 9A-9B illustrates examples of sleeve-puncturing assemblies in accordance with various embodiments.
Figure 9B:
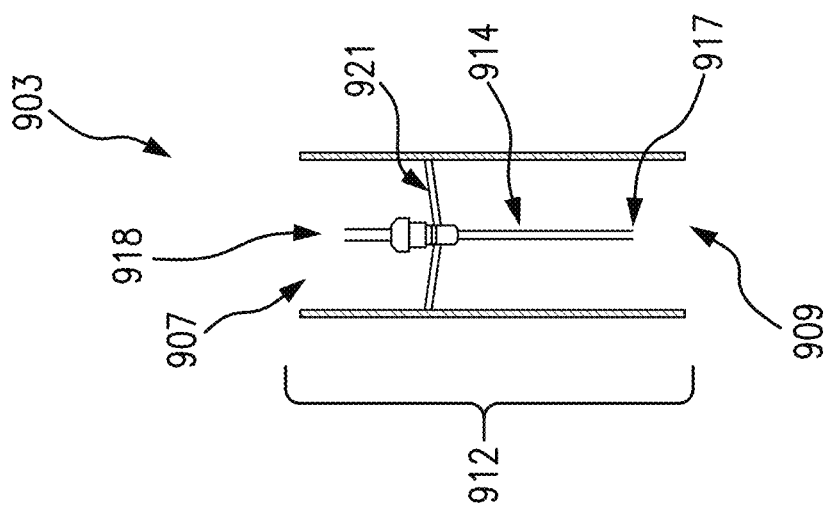

FIGS. 9A-9B illustrates example sleeve-puncturing assemblies according to a seventh embodiment and an eighth embodiment. In the seventh and eighth embodiments, the sleeve-puncturing assembly 903, 905 includes a sleeve 912 and a hollow conduit 914. The sleeve 912, in the seventh and eighth embodiments, can be a cylindrical barrel having an open end 909 for receiving a blood collection container and another open end 907 for receiving the blood transfer container. The hollow conduit 914 is coupled to the sleeve 912 and includes a first end 917 configured to pierce a top of the blood collection container and a second end 918 configured to pierce a top of the blood transfer container. The hollow conduit 914 can be permanently affixed to at least one longitudinal portion of the sleeve 912, and once affixed, may not be removed or otherwise retracted. As illustrated, the hollow conduit 914 can be affixed to the walls of the sleeve 912 via supports 921 (e.g., beams) that include one end coupled to the sleeve 912 and another end coupled to the hollow conduit 914. The supports 921 can be formed of a variety of material, such as plastic, metal and glass.

As previously described, the first end 917 of the hollow conduit 914 can contact plasma or serum of a blood sample contained within the blood collection container. The blood transfer container has a negative pressure inside sufficient to pull a predetermined amount of plasma or serum from the blood collection container. The blood collection container and blood transfer container, according to the seventh and eighth embodiments, can be the same containers as previously described and illustrated in FIGS. 1A and 1B. In the seventh and eighth embodiments, the first end 917 and the second end 918 of the hollow conduit 914 are enclosed respectively by the sleeve 912. The hollow conduit 914 extends proximally within the sleeve 912 (e.g., the internal space formed by the longitudinal portions/walls), and the walls of the sleeve 912 extend past the first end 917 and the second end 918 of the hollow conduit 914. Although embodiments are not so limited and in some embodiments, the walls may not extend past one or more of the ends 917, 918 of the hollow conduit 914, which can be protected by a removable cap and/or a collar. Further, in the eighth embodiment as depicted by FIG. 9B, the sleeve-puncturing assembly 905 includes a collar 923 that encloses the second end 918 of the hollow conduit 914, and is configured to engage the blood transfer container, as previously described in connection with FIG. 1A.

As illustrated by the eighth embodiment, the hollow conduit 914 can be affixed to the sleeve via supports 921 (e.g., beams) that are coupled to the longitudinal portions/walls (e.g., within a hollow portion) of the sleeve 912 on one end and coupled to the hollow conduit on another end. A plurality of supports, which may form a cross shape (e.g., an "X" shape with the hollow conduit 914 in the middle of the "X"), can be used.

Although the above second-eighth embodiment describes that the second end of the hollow conduit pierces the top of the blood transfer container, such embodiments are not so limited and can include the second end of the hollow conduit otherwise engaging the blood transfer container. For example, and as previously described, the blood transfer container can have a pressure-adjusting mechanism which is used to generate the negative pressure. In such embodiments, the blood transfer container includes a (cylinder) barrel with a plunger or piston on one end and another end for engaging the sleeve-puncturing assembly, as described-above. The other end can include a sealed top and/or nozzle (which may also include a "sealed nozzle") that couples to the second end of the hollow conduit. In response to pulling the plunger or piston in a direction away from the end with the top or nozzle, the negative pressure is generated inside the barrel of the blood transfer container. The negative pressure can be generated prior to or after engaging the blood transfer container with the sleeve-puncturing assembly. Responsive to engaging the blood transfer container with the sleeve-puncturing assembly, and while the first end of the hollow conduit is in contact with the plasma or serum in the blood collection container, the predetermined amount of plasma or serum is drawn into the blood transfer container.

In such embodiments, the order of engaging or coupling the various components of the blood transfer apparatus can include the same or a different order than previously described. For example, in various embodiments, the sleeve-puncturing assembly is first engaged with the blood collection container and then engaged with the blood transfer container, as previously described. The negative pressure can be generated prior to or after engaging the blood transfer container to the sleeve-puncturing assembly. In other embodiments, the sleeve-puncturing assembly is first engaged with the blood transfer container and/or the blood transfer container is formed as part of the sleeve-puncturing assembly (e.g., is temporarily affixed and can be detached from the sleeve-puncturing assembly), and then engages the blood collection container. The negative pressure can be generated prior to or after engaging the blood collection container to or with the sleeve-puncturing assembly. The various method embodiments can include the above-described variations, such as separating cell fraction from plasma or serum of the blood sample, user or automated arm placing the sleeve-puncturing assembly over the blood collection and/or engaging the collar to a blood transfer container, and the various embodiments of the sleeve-puncturing assembly including the optional collar, removable caps, sealed tops or nozzles, etc. Further, the method embodiments may include various combinations and subsets of the above-listed steps.

As may be appreciated, the particular lengths/distances of the walls of the sleeve-puncturing assembly can be varied in various embodiments and are not limited to that illustrated by FIGS. 1A-1B, 2A-2B, and/or 5A-9B. Further, the sleeves can be a variety of shapes and are not limited to cylinder shaped barrels. For example, in some embodiments, the sleeves is other tubular shapes, such as a rectangular tube. The various embodiments described herein can include features described in other embodiments and in various combinations. For example, the second-eighth embodiments can include the at least one protrusion arranged about the circumference of the sleeve proximal to the open end of the sleeve, as previous described in connection with FIGS. 1A-2F.

The various figures herein illustrate example sleeve-puncturing assemblies. The sleeves are illustrated, for clarity purposes, as two-dimensional cup-shapes such that placement of the sleeve-puncturing assemblies over containers can be shown. As would be appreciated by one of ordinary skill, and as specifically illustrated by FIGS. 2A-2F, the sleeves include three-dimensional structures (e.g., a cylindrical barrel) having the open end and the other end, as described throughout the detailed description.

Various embodiments are implemented in accordance with the underlying Provisional Application (Ser. No. 62/564,684), entitled "Sleeve-Puncturing Assemblies and Methods Thereof", filed Sep. 28, 2017, to which benefit is claimed and is fully incorporated herein by reference. For instance, embodiments herein and/or in the Provisional Application may be combined in varying degrees (including wholly). For information regarding details of these and other embodiments, applications and experiments (as combinable in varying degrees with the teachings herein), reference may be made to the teachings and underlying references provided in the Provisional Application which forms part of this patent document and is fully incorporated herein.

Various embodiments described above may be implemented together and/or in other manners. One or more of the items depicted in the present disclosure can also be implemented separately or in a more integrated manner, or removed and/or rendered as inoperable in certain cases, as is useful in accordance with particular applications. In view of the description herein, those skilled in the art will recognize that many changes may be made thereto without departing from the spirit and scope of the present disclosure. The term "engaged", "engage", "engaging" includes or refers to joining of two or more components, but is not limited to a direct connection or touching of the two or more components (e.g., the two components do not have to be directly connected). As used herein, the term "coupling", "couple", or "coupled" is interchangeably used with the term "engaging", "engage" or "engaged." In some embodiments, two (or more) components that are coupled or engaged can be directly coupled or engaged, as illustrated by various figures herein.

Based upon the above discussion and illustrations, those skilled in the art will readily recognize that various modifications and changes may be made to the various embodiments without strictly following the exemplary embodiments and applications illustrated and described herein. Such modifications do not depart from the true spirit and scope of various aspects of the invention, including aspects set forth in the provisional claims.

What is claimed is:

1. A blood transfer apparatus comprising a sleeve-puncturing assembly, the sleeve-puncturing assembly comprising:
   a) a hollow conduit comprising a proximal end comprising a collar configured and arranged to engage with a blood transfer container having a negative pressure; and
   b) a sleeve configured and arranged with longitudinal portions to be placed over or engage a blood collection container, the sleeve comprising:
      i) an open end configured and arranged to engage with a portion of the blood collection container;
      ii) a closed end configured and arranged to provide containment of the blood collection container while the open end is engaged with the portion of the blood collection container;
      iii) a lateral portion of the sleeve configured and arranged to provide support to the hollow conduit; and
      iv) a plurality of protrusions arranged about the circumference of the sleeve and proximal to the open end of the sleeve;
   wherein the hollow conduit and the longitudinal portions of the sleeve are configured and arranged to engage with the blood collection container and wherein the negative pressure is sufficient to pull a predetermined amount of plasma or serum from the blood collection container.

2. The apparatus of claim 1, wherein the hollow conduit comprises:
   a distal end configured and arranged to pierce an upper portion of the blood collection container and to extend a sufficient distance to contact a portion of a blood sample contained within the blood collection container.

3. The apparatus of claim 2, wherein the longitudinal portions of the sleeve comprise walls extending from the closed end to the open end and the walls of the sleeve extend past the distal end of the hollow conduit.

4. The apparatus of claim 1, wherein the longitudinal portions of the sleeve comprise walls extending from the closed end to the open end, and the hollow conduit extends toward the open end of the sleeve.

5. The apparatus of claim 1, wherein the plurality of protrusions jut out from an interior surface of the sleeve and toward a center portion of the sleeve.

6. The apparatus of claim 1, wherein at least one of the blood collection container and the blood transfer container comprises an upper portion, which comprises a sealed stopper formed of a rubber or other type of elastomer that is configured and arranged to maintain seal of the blood collection container and/or the blood transfer container, thereby maintaining the negative pressure inside the blood transfer container.

7. A blood transfer apparatus, comprising:
a) a blood transfer container comprising a negative pressure that is sufficient to pull a predetermined amount of plasma or serum from the blood collection container, and an upper portion configured and arranged to maintain the negative pressure inside the blood transfer container; and
b) a sleeve-puncturing assembly comprising:
 i) a sleeve configured and arranged with longitudinal portions to be placed over or engage a blood collection container comprising an upper portion, the sleeve comprising:
  an open end configured and arranged to engage with a portion of the blood collection container;
  a closed end configured and arranged to provide containment of the blood collection container while the open end is engaged with the portion of the blood collection container;
  a lateral portion of the sleeve configured and arranged to provide support to the hollow conduit; and
  a plurality of protrusions arranged about the circumference of the sleeve that jut out from the longitudinal portions of the sleeve and toward a center portion of the sleeve; and
 ii) a hollow conduit comprising:
 a distal end configured and arranged to pierce the upper portion of the blood collection container and to extend a distance sufficient to contact a portion of a blood sample contained within the blood collection container; and
 a proximal end configured and arranged to pierce the upper portion of the blood transfer container to cause the blood transfer container to pull the predetermine amount of plasma or serum from the blood collection container, wherein the proximal end comprises a collar configured and arranged to engage with the blood transfer container;
wherein the hollow conduit and the longitudinal portions of the sleeve are configured and arranged to engage with the blood collection container, and while engaged, to pull the predetermined amount of plasma or serum from the blood collection container based on the negative pressure inside the blood transfer container.

8. The blood transfer apparatus of claim 7, wherein the upper portion of the blood transfer container comprises a sealed top that is configured and arranged to be pierced by the collar of the hollow conduit, resulting in the negative pressure causing the plasma or serum to pull therein.

9. The blood transfer apparatus of claim 7, wherein the blood sample comprises separated layers of a cell fraction and the plasma or serum.

10. The blood transfer apparatus of claim 7, wherein the longitudinal portions of the sleeve are configured and arranged to extend from the upper portion of the blood collection container toward a bottom portion of the blood collection container while engaged with the blood collection container, and wherein the distal end of the hollow conduit extends into a hollow portion of the blood collection container sufficient to contact the plasma or serum of the blood sample.

11. The blood transfer apparatus of claim 9, wherein the hollow conduit does not extend or otherwise contact the cell fraction of the blood sample.

12. The blood transfer apparatus of claim 7, wherein responsive to the open end of the sleeve engaging the blood collection container, the distal end of the hollow conduit is configured and arranged to pierce the upper portion of the blood collection container and to contact the plasma or serum of the blood sample.

13. A method for transferring blood from a blood collection container to a blood transfer container, the method comprising:
a) placing a sleeve-puncturing assembly over or engaging with a blood collection container comprising plasma or serum separated from a cell fraction, thereby piercing a sealed upper portion of the blood collection container with a distal end of a hollow conduit and contacting the plasma or serum with the first end of the hollow conduit, wherein the sleeve-puncturing assembly comprises:
 i) the hollow conduit comprising the distal end and a proximal end comprising a collar configured and arranged to engage with a blood transfer container having a negative pressure; and
 ii) a sleeve comprising an open end, a closed end, longitudinal portions configured and arranged to be placed over or engage with the blood collection container, a lateral portion configured and arranged to provide support to the hollow conduit, and a plurality of protrusions arranged about the circumference of the sleeve that jut out from the longitudinal portions of the sleeve and toward a center portion of the sleeve;
b) engaging the sleeve-puncturing assembly with the blood transfer container while the distal end of the hollow conduit is in contact with the plasma or serum, the blood transfer container comprising a pressure adjusting mechanism to provide a negative pressure that is sufficient to pull a predetermined amount of plasma or serum from the blood collection container and a sealed upper portion configured and arranged to seal the negative pressure inside; and
c) in response to engaging to the blood transfer container:
piercing the sealed upper portion of the blood transfer container with the second end of the hollow conduit; and
pulling the predetermined amount of plasma or serum into the blood transfer container from the blood collection container via the negative pressure.

14. The method of claim 13, wherein engaging the sleeve-puncturing assembly with the blood transfer container further comprises: engaging the collar with the blood transfer container while the first end of the hollow conduit is in contact with the plasma or serum.

15. The method of claim 13, further comprising:
collecting a blood sample in a blood collection container comprising the sealed upper portion; and
separating a cell fraction from the plasma or serum of the blood sample.

\* \* \* \* \*